US010016160B2

(12) United States Patent
Rahko et al.

(10) Patent No.: US 10,016,160 B2
(45) Date of Patent: Jul. 10, 2018

(54) WRIST BAND FOR MEASURING HEART RATE OF THE USER

(71) Applicant: Polar Electro Oy, Kempele (FI)

(72) Inventors: Juho Rahko, Oulu (FI); Erkki Hinkola, Oulu (FI); Lauri Lumme, Oulu (FI); Mikko Repka, Oulu (FI)

(73) Assignee: Polar Electro Oy, Kempele (FI)

( * ) Notice: Subject to any disclaimer, the term of this patent is extended or adjusted under 35 U.S.C. 154(b) by 309 days.

(21) Appl. No.: 14/847,659

(22) Filed: Sep. 8, 2015

(65) Prior Publication Data

US 2017/0065224 A1 Mar. 9, 2017

(51) Int. Cl.
*A61B 5/00* (2006.01)
*A61B 5/024* (2006.01)
*A61B 5/026* (2006.01)

(52) U.S. Cl.
CPC .......... *A61B 5/681* (2013.01); *A61B 5/02405* (2013.01); *A61B 5/02427* (2013.01); *A61B 5/02438* (2013.01); *A61B 5/6824* (2013.01); *A61B 5/7405* (2013.01); *A61B 5/7435* (2013.01); *A61B 5/7455* (2013.01); *A61B 5/7475* (2013.01); *A61B 5/0261* (2013.01)

(58) Field of Classification Search
CPC ....... G04B 37/1486; G06F 1/16; G06F 1/163; G04G 21/00; A45F 2005/008; A45F 2200/0525; A45F 5/00; A45F 2200/0516; G06Q 10/0639; G06Q 50/22; A61B 5/681; A61B 5/02438; A61B 5/742; A61B 2562/0233; A61B 5/02427; A61B 5/72; A61B 5/486; A61B 5/6885; A61B 5/02416; A61B 5/7221; A61B 5/7278; A61B 5/02405; A61B 5/1118
See application file for complete search history.

(56) References Cited

U.S. PATENT DOCUMENTS

2014/0156196 A1 6/2014 Martinez et al.
2015/0105221 A1 4/2015 Roush et al.

FOREIGN PATENT DOCUMENTS

CN 104146771 A 11/2014
WO WO 2010/126821 A1 11/2010

OTHER PUBLICATIONS

European Search Report issued in European Application No. EP 16186814 dated Jan. 27, 2017.

*Primary Examiner* — Harshad R Patel
*Assistant Examiner* — Brandi Hopkins
(74) *Attorney, Agent, or Firm* — FisherBroyles, LLP

(57) ABSTRACT

A wristband, an electronics module, and a wrist device are disclosed. The wristband and the electronics module form the modular wrist device. The electronics module, when mounted to the wristband, stiffens a structure of at least a portion of the wrist device in order to enable the wrist device to firmly attach against a wrist of a user and to enable optical heart activity measurement by the electronics module.

31 Claims, 13 Drawing Sheets

510 DETERMINE THAT THE ELECTRONICS MODULE IS NOT USED FOR A PREDETERMINED TIME

520 BASED ON THE DETERMINATION, PERFORMING AT LEAST ONE OF DIMMING THE DISPLAY, TURNING OFF THE DISPLAY

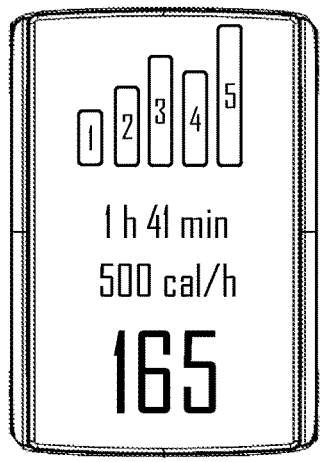

Fig. 7B

810 DETECT AT LEAST ONE GESTURE PERFORMED BY THE USER

↓

820 BASED ON THE DETECTED AT LEAST ONE GESTURE, CAUSE A FUNCTION TO BE PERFORMED ON THE ELECTRONICS MODULE

Fig. 8

910 DETERMINE THAT AT LEAST ONE EXTERNAL SENSOR IS COUPLED WITH THE ELECTRONICS MODULE

↓

920 PROCESS AT LEAST ONE OF THE HEART ACTIVITY METRIC, THE MOTION METRIC BASED AT LEAST PARTLY ON DATA FROM THE AT LEAST ONE EXTERNAL SENSOR

Fig. 9

WRIST BAND FOR MEASURING HEART RATE OF THE USER

BACKGROUND

Field

This invention relates to wrist devices.

Description of the Related Art

Wrist devices are becoming more popular among users for different purposes. One example is to use wrist devices for physical activity measurement, such as measuring optically heart rate from a wrist of the user. Therefore, solutions making the optical heart activity measurement more effortless and/or enhanced may be beneficial.

SUMMARY

According to an aspect, there is provided the subject matter of the independent claims.

According to an aspect, there is provided a wristband comprising: a first, second and third portions, the third portion being situated between the first and second portions, the first, second and third portions forming one integral entity being elastic, wherein the first and second portions are configured to be mechanically connected to each other in order to enable detachable and adjustable attachment of the wristband to a wrist of a user, and wherein the third portion comprises a holder configured to enable detachable mounting of an electronics module to the wristband, the electronics module being capable of optical heart activity measurement, the holder being adapted and dimensioned to produce a spring force to the electronics module in order to keep the electronics module in the holder, and to enable the electronics module, when mounted to the wristband, to stiffen a structure of the third portion in order to enable the wristband to firmly attach against the wrist of the user and to enable the optical heart activity measurement with the electronics module.

In an embodiment, the wristband further comprises: at least one pin situated at the first portion, the at least one pin comprising at least one bulge; and at least one opening situated at the second portion, wherein the at least one pin is configured to at least partially penetrate the at least one opening, the at least one bulge being adapted and dimensioned such that the at least one bulge detachably locks the at least one pin to the at least one opening.

In an embodiment, the at least one opening of the second portion comprises a hollow adapted and dimensioned to receive the at least one bulge.

In an embodiment, the at least one pin comprises a base plate.

In an embodiment, the at least one pin, when attached to the first portion, is substantially perpendicular to the first portion.

In an embodiment, the wristband further comprises: at least one opening situated at the first portion enabling a detachable attachment of the at least one pin to the first portion.

In an embodiment, the at least one pin is enabled to penetrate from a side of the first portion to an opposite side of the first portion through the at least one opening of the first portion, and wherein said at least one opening comprises a first hollow adapted and dimensioned to receive the base plate of the pin on said side of the first portion.

In an embodiment, a depth of the first hollow is substantially same as a thickness of the base plate, and wherein an area of a bottom of the first hollow is substantially same as an area of the base plate that is configured to be placed against the bottom of the first hollow.

In an embodiment, the second portion comprises a buckle adapted and dimensioned such that the first portion is enabled to slide through the buckle.

In an embodiment, the holder comprises at least one hollow for receiving at least one button of the electronics module.

In an embodiment, the holder comprises at least one protrusion arranged together with the at least one hollow, the at least one protrusion configured to enable mechanical energy transfer from the at least one protrusion to the at least one button of the electronics module.

In an embodiment, the holder comprises a first and a second mounting elements, the mounting elements being less elastic compared with the wristband.

In an embodiment, at least one of the first and second mounting elements comprises a hollow for the electronics module.

In an embodiment, at least one of the first and second mounting elements comprises an alignment hollow for an alignment element of the electronics module.

In an embodiment, the first and second mounting elements are facing each other.

In an embodiment, the first and second mounting elements each comprise a claw enabling the mounting of the electronics module.

According to an aspect, there is provided an electronics module comprising: an optical heart activity circuitry configured to measure heart activity of a user; a processing circuitry configured to obtain heart activity measurement data, and to process said data into a heart activity metric characterizing a heart activity of the user; a body enclosing at least partly the optical heart activity circuitry and the processing circuitry, the body configured to enable mounting of the electronics module to a holder of a wristband, the body being adapted and dimensioned so that, when mounted to the holder, a measuring head of the optical heart activity circuitry is enabled to be placed against a wrist of the user.

In an embodiment, the electronics module further comprises: a communication circuitry configured to enable communication with an external device.

In an embodiment, the electronics module further comprises: an antenna structure electrically coupled with the communication circuitry, the antenna structure being situated on at least one edge area of the electronics module.

In an embodiment, the electronics module further comprises: a cable port configured to receive an external cable, wherein the cable port enables at least one of a charging a battery of the electronics module, transferring data between the electronics module and the external device.

In an embodiment, the electronics module further comprises: a user interface configured to enable the user to interact with the electronics module.

In an embodiment, the user interface comprises a touch display.

In an embodiment, the user interface comprises at least one button.

In an embodiment, the at least one button comprises a multifunction button, and wherein pressing the multifunction button causes at least one of the following: switching the electronics module on, switching the electronics module off, pairing the electronics module with the external device, changing of a current display element to a previous display element, pausing a physical activity recording, stopping the physical activity recoding.

In an embodiment, the multifunction button is a mechanical button.

In an embodiment, the body comprises a first and a second mounting counterparts corresponding to a first and a second mounting elements of the holder of the wristband.

In an embodiment, the first and second mounting counterparts each comprise a hollow corresponding to claws of the first and second mounting elements of the holder of the wristband.

In an embodiment, the processing circuitry is configured to: obtain at least one of the heart activity measurement data, the motion measurement data; and determine intensity of the physical activity performed by the user based on the obtained data.

In an embodiment, the processing circuitry is further configured to: obtain a plurality of intensity zones; based on the intensity of the physical activity, determine a time on an intensity zone of the plurality of intensity zones; and increase an intensity zone time based on said determination.

According to an aspect, there is provided a wrist device comprising: a wristband being substantially elastic and forming one integral entity, the wristband comprising a first, second and third portions, the third portion being situated between the first and second portions, wherein the first and second portions are configured to mechanically connect to each other in order to enable detachable and adjustable attachment of the wrist device to a wrist of a user; and an electronics module comprising an optical heart activity sensor configured to measure heart activity of the user and a processing circuitry configured to obtain heart activity measurement data from the optical heart activity sensor, and to process said data into a heart activity metric characterizing a heart activity of the user, wherein the third portion of the wristband comprises a holder configured to enable detachable mounting of the electronics module to the wristband, the holder and the electronics module being adapted and dimensioned so that the holder produces a spring force to the electronics module in order to keep the electronics module in the holder, the electronics module, when mounted to the wristband, stiffening a structure of the third portion in order to enable the wrist device to firmly attach against the wrist of the user and to enable the optical heart activity measurement by the electronics module.

Some embodiments are defined in the dependent claims. One or more examples of implementations are set forth in more detail in the accompanying drawings and the description below. Other features will be apparent from the description and drawings, and from the claims.

BRIEF DESCRIPTION OF THE DRAWINGS

In the following embodiments will be described in greater detail with reference to the attached drawings, in which

FIG. 7B illustrates an embodiment of the invention;
FIG. 8 illustrates a block diagram according to an embodiment;
FIG. 9 illustrates a block diagram according to an embodiment.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
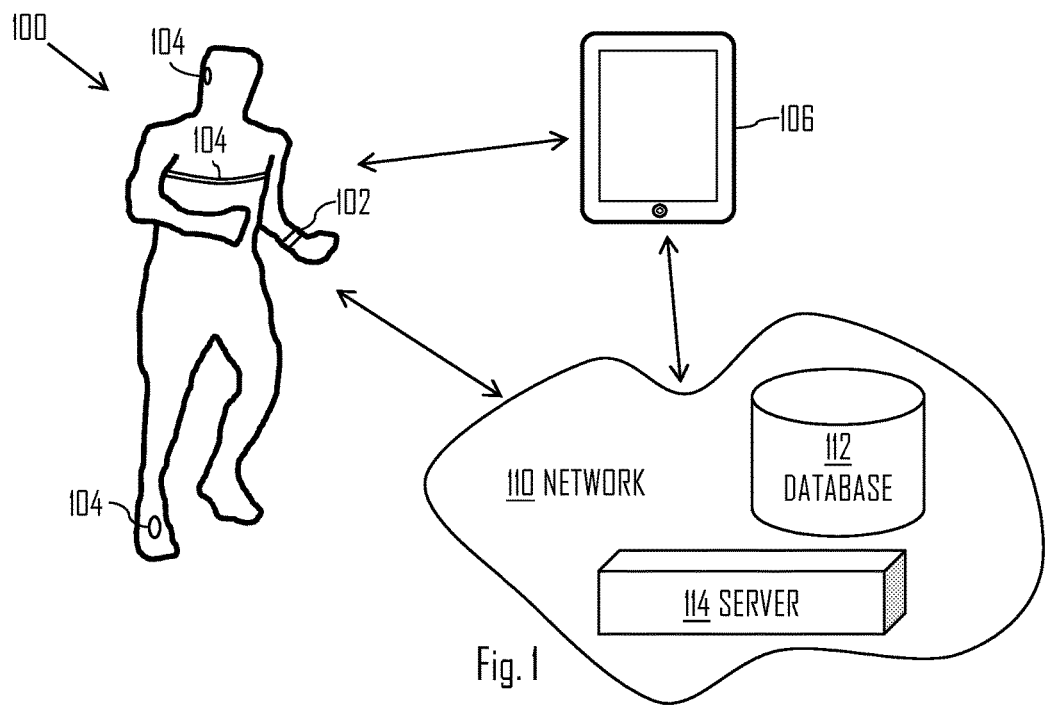
FIG. 1 illustrates a physical activity measurement scenario to which embodiments of the invention may be applied.

FIG. 1 illustrates a heart activity measurement system to which embodiments of the invention may be applied. Referring to FIG. 1, a user 100 may wear a wearable device 102, such as a wrist device 102. The wrist device 102 may be, for example, a smart watch, a smart device, sports watch, and/or an activity tracking apparatus.

In an embodiment, the wrist device 102 is an activity tracking apparatus. This may mean that said apparatus may be worn in other parts of the user 100, such as but not limited to forearm, bicep area, neck, forehead, and/or leg.

The wrist device 102 may be used to monitor physical activity of the user 100 by using data from internal sensor(s) comprised in the wrist device 102 and/or data from external sensor device(s) 104. It may be possible to receive physical activity-related information from a network 110, as the network may comprise, for example, physical activity-related information of the user 100 and/or some other user(s). Thus, the wrist device 102 may be used to monitor physical activity-related information of the user 100 and/or the other user(s). Naturally, one or more of the external sensor device(s) 104 may be worn by the other user(s), and thus information received from said one or more sensor device(s) 104 may be monitored from the wrist device 102 by the user 100.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) may also be used.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating in the cellular network.

The wrist device 102 may be used to monitor activity and/or inactivity of the user 100. The wrist device 102 may comprise a heart activity circuitry configured to determine heart activity of the user 100, such as heart rate, Heart Beat Interval (HBI) and/or Heart Rate Variability (HRV), for example. The heart activity circuitry may comprise an optical heart activity sensor, such as a PPG (photoplethysmography) sensor, configured to measure heart activity of the user 100. The optical heart activity sensor may detect the heart activity of the user 100 by optical heart rate measurement, which may comprise sending a light beam towards skin of the user 100 and measuring the bounced and/or emitted light from the skin of the user 100. The light beam may alter when travelling through veins of the user 100 and the alterations may be detected by the optical heart rate activity sensor. By using the detected data, the wrist device 102, may determine heart activity of the user 100, such as heart rate for example.

The heart activity circuitry may comprise a bioimpedance sensor, wherein the bioimpedance sensor is configured to measure heart activity of the user 100. The bioimpedance measurement may be based on transmitting a radio signal into the skin of the user, and observing changes in the radio signal due to impedance changes caused by, for example, blood volume changes. Thus, heart activity of the user 100 may be determined by the wrist device 102 from the data produced by the bioimpedance sensor.

Further, besides these types of heart activity sensors, also other types of biosignal measurement sensors may be embedded into the heart activity circuitry. These types include but are not limited to the following: a Laser Doppler-based blood flow sensor, a magnetic blood flow sensor, an Electromechanical Film (EMFi) pulse sensor, a polarization blood flow sensor, an Electrocardiography (EKG) sensor comprising at least one electrode.

It also needs to be noted that the heart activity circuitry may produce raw measurement data of the heart activity and/or it may process the measurement data into heart activity information, such as heart rate for example. The sensor(s) in the heart activity circuitry may comprise data processing capabilities. Also, the wrist device may comprise a processing circuitry configured to obtain the heart activity measurement data from the heart activity circuitry and to process said data into heart activity information, such as a heart activity metric characterizing the heart activity of the user. For example, the measurement data of the optical heart activity sensor may be used, by the processing circuitry, to determine heart rate, HRV and/or HBI of the user 100. Further, the raw measurement data and/or processed information may be processed by the wrist device 102 and/or transmitted to an external device, such as the portable electronic device 106.

In an embodiment, the wrist device 102 may comprise a motion circuitry configured to measure motion induced by the user 100 to the wrist device 102 by moving hand (or other body parts to which the wrist device is attached to) in which the user 100 wears the wrist device 102. The motion circuitry may use other motion data, such as location data of the user, to determine motion of the user 100. For example, the motion circuitry may comprise a GPS receiver for receiving GPS data. The GPS data may be used, by the wrist device 102, to determine motion of the user 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the heart activity measurement system may further comprise the external sensor device(s) 104 used by the user 100. The external sensor device(s) 104 may be worn by the user 100. The external sensor device(s) 104 may comprise sensors, such as a heart rate transmitter, heart rate sensor, a stride sensor, a positioning sensor, a cadence sensor and a power sensor, to mention a few. The heart rate transmitter may comprise at least one electrical, optical and/or bioimpedance sensor to measure heart activity of the user 100. The electrical sensor(s) may be, for example, based on EKG measurement. The positioning sensor may comprise a GPS, a magnetometer and/or a Bluetooth sensor. Thus, the positioning may be based on, for example, GPS location and/or Bluetooth location. The magnetometer may provide direction data based on magnetic fields on earth and/or inside structures.

The external sensor device(s) 104 may comprise a head sensor, wherein the head sensor may be configured to measure heart activity of the user 100. The head sensor may be, for example, an ear sensor which may be placed in physical connection with an ear and/or ears of the user 100. The placement may be similar to placing earplug headphones, for example. Another example may be to use a clip mechanism and/or glue-like material for the physical connection. The head sensor may utilize optical measurement and/or bioimpendace measurement for the heart rate measurement, for example. In an embodiment, the ear sensor is an in-ear sensor.

In an embodiment, the head sensor is comprised in glasses. In such case the head sensor may be comprised in earpiece(s) of the glasses, for example.

In an embodiment, the head sensor is comprised in headphones and/or earphones.

In an embodiment, the external sensor device(s) 104 comprise at least one of a cadence sensor, a speed sensor, a power sensor used in a bicycle.

The external sensor device(s) 104 may transmit the sensor data to the wrist device 102, to the portable electronic device 106 and/or to a server 114, residing in a network 110, of the heart activity measurement system. The wrist device 102, the portable electronic device 106 and/or the server 114 may receive the sensor data. Similarly, the wrist device 102 may transmit the heart activity data, provided by the heart activity circuitry 352, the motion sensor data, provided by the motion circuitry 354, and/or some other data to the portable electronic device 106 and/or the server 114. The wrist device 102, the portable electronic device 106 and/or the server 114 may comprise at least one processor configured to process the received external sensor data, the heart activity data and/or the motion data into a set of metrics describing physical activity of the user, such as heart rate, energy expenditure and/or travelled distance, for example.

The external sensor device(s) 104, the wrist device 102, the portable electronic device 106 and/or the server 114 may each further comprise a communication circuitry, such as wireless communication circuitry, configured to enable sensor data transfer between the external sensor device(s) 104, wrist device 102, portable electronic device 106 and/or the server 114.

Further, the wrist device 102 and/or the portable electronic device 106 may comprise a memory, wherein the memory may be used by the devices to store the data from different sensor device(s). The server 114 may use a database 112, such as a training database, to store the said data. The database 112 may reside in the network 110.

In an embodiment, the external sensor device(s) 104 are comprised in the wrist device 102.

In an embodiment, the wrist device 102 comprises at least one of the following sensors: a temperature sensor, a positioning sensor and a pressure sensor. The positioning sensor may utilize GPS and/or Bluetooth information for locating the user 100. Further, the positioning sensor may comprise a magnetometer. Thus, the positioning sensor may be comprised in the motion circuitry, for example.

Wrist devices may be used to monitor physical activity of the user 100. However, normally the wrist devices, such as activity tracking apparatuses, may be designed such that their usability may be lacking in some areas. For example, battery of the wrist device may be such that it needs to be charged every day at least if position, motion and/or heart activity is monitored regularly.

There is provided a solution to enhance the usability of the wrist device 102 by designing and/or manufacturing the wrist device 102 to be modular. The modular structure may enable the user 100, for example, to charge the battery of the wrist device 102 when the strap is still worn by the user. For example, the wrist device 102 may comprise an electronics module that may be detachably attached to the wrist strap of the wrist device 102. This may further, for example, enable the user 100 to use different wrist straps (i.e. different color, shapes) and/or different electronics modules (i.e. different functions, sensors, design, color, shape). Thus, the attractiveness of the wrist device 102 may be improved by using the modular structure.

Figure 2A:
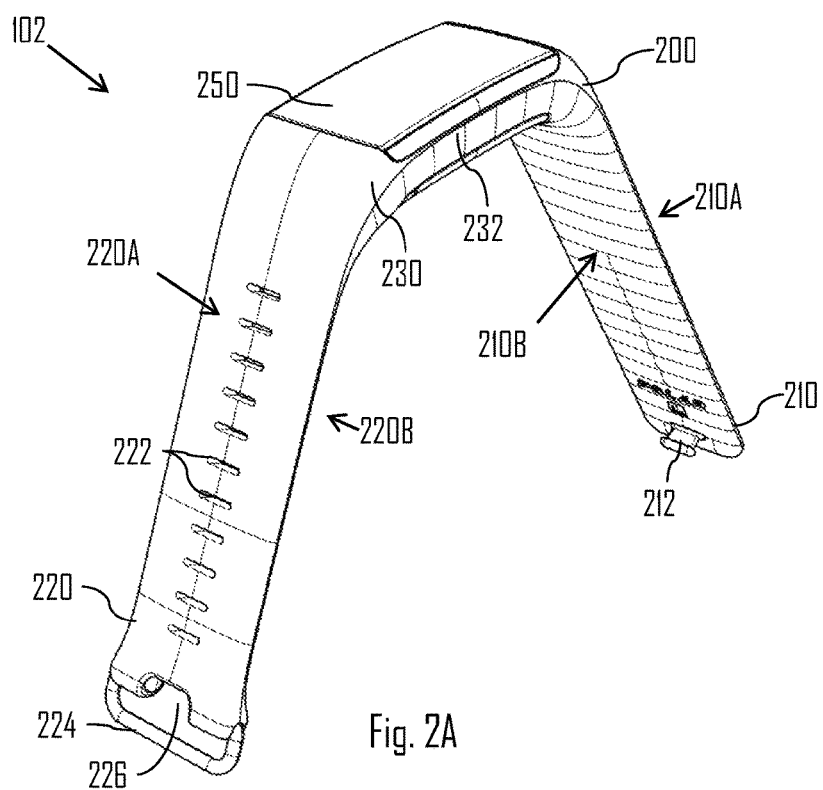
FIGS. 2A to 2C illustrate some embodiments.
Figure 2B:
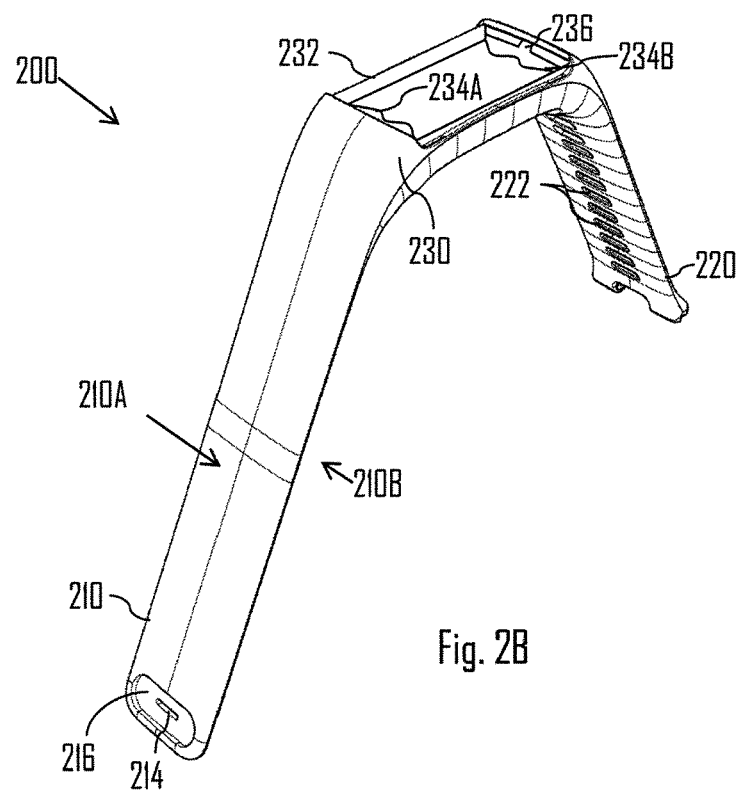
Figure 2C:
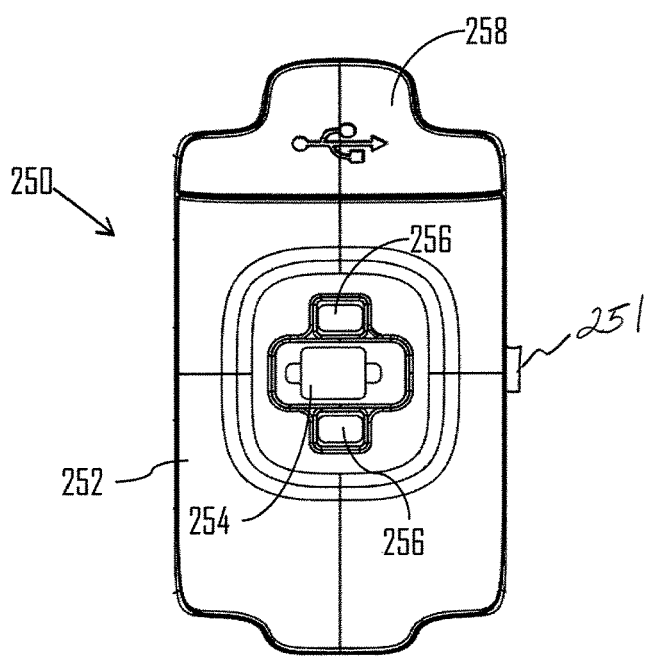

FIGS. 2A to 2C illustrate some embodiments of the invention. Referring to FIG. 2A, the wrist device 102 comprises a wristband 200 being substantially elastic and forming one integral entity, the wristband 200 comprising a first portion 210, a second portion 220 and third portion 230, the third portion 230 being situated between the first and second portions 210, 220, wherein the first and second portions 210, 220 are configured to mechanically connect to each other in order to enable detachable and adjustable attachment of the wrist device 102 to a wrist of the user 100. In an embodiment, the connection is at least partially magnetic. In an embodiment, the connection is magnetic. Thus, the first and second portions 210, 220 may be magnetically connected to each other.

The wrist device 102 further comprises an electronics module 250 comprising an optical heart activity sensor configured to measure heart activity of the user 100 and a processing circuitry configured to obtain heart activity measurement data from the optical heart activity sensor, and to process said data into a heart activity metric characterizing a heart activity of the user 100.

Further, the third portion 230 of the wristband 200 comprises a holder 232 configured to enable detachable mounting of the electronics module 250 to the wristband 200, the holder 232 and the electronics module 250 being adapted and dimensioned so that the holder 232 produces a spring force to the electronics module 250 in order to keep the electronics module 250 in the holder 232. The electronics module 250, when mounted to the wristband 200, stiffens a structure of the third portion 230 in order to enable the wrist device 102 to firmly attach against the wrist of the user 100, and thus enables the optical heart activity measurement by the electronics module 250. Thus, the electronics module 250 may make the wrist device 102 or more specifically, the wristband 200 such that the wrist device 102 may be attached firmly against the wrist of the user 100 even though the wristband 200 may be elastic and/or flexible. The electronics module 250 may be substantially rigid, inflexible and/or inelastic.

For example, the wristband 200 may be at least partially made of soft material. This may cause the wristband 200 to be comfortable to wear. However, the attachment to the wrist of the user 100 may require firm structure from the wrist device 102. Thus, the electronics module 250 may, when mounted to the wrist band 200, stiffen the structure of the wrist device 102 and/or at least a portion of the wristband, as explained above. Thus, together the wristband 200 and the electronics module 250 may provide comfortable and usable wrist device 102 for optical heart activity measurement.

In an embodiment, there is provided the wristband 200 as shown in FIG. 2B, the wristband 200 comprising the first, second and third portions 210, 220, 230, the third portion 230 being situated between the first and second portions 210, 220, the first, second and third portions 210, 220, 230 forming one integral entity being elastic. The first and second portions 210, 220 may be configured to be mechanically connected to each other in order to enable detachable and adjustable attachment of the wristband 200 to the wrist of the user 100. The third portion 230 may comprise the holder 232 configured to enable detachable mounting of an electronics module, such as the electronics module 250, to the wristband 200, the electronics module being capable of optical heart activity measurement. The holder 232 may be adapted and dimensioned to produce a spring force to the electronics module in order to keep the electronics module in the holder 232, and to enable the electronics module, when mounted to the wristband 200, to stiffen a structure of the third portion 230 in order to enable the wristband 200 to firmly attach against the wrist of the user 100 and to enable the optical heart activity measurement with and/or by the electronics module.

In an embodiment, there is provided the electronics module 250 as shown in FIG. 2C, the electronics module 250 comprising an optical heart activity circuitry configured to measure heart activity of the user 100. The electronics module 250 may further comprise a processing circuitry configured to obtain heart activity measurement data, and to process said data into a heart activity metric characterizing a heart activity of the user 100. The processing circuitry may obtain the heart activity measurement data from the optical heart activity circuitry and/or from the external sensor device(s) 104, for example. The electronics module may further comprise a body 252 enclosing at least partly the optical heart activity circuitry and the processing circuitry, the body configured to enable mounting of the electronics module to a holder, such as the holder 232, of a wristband, such as the wristband 200, the body 252 being adapted and dimensioned so that, when mounted to the holder, a measuring head 254, 256 of the optical heart activity circuitry is enabled to be placed against the wrist of the user 100.

In an embodiment, the measuring head 254, 256 comprises at least one light source 256, such as a Light Emitting Diode (LED), and at least one detector 254, such as a matrix detector and/or photodiode. The measuring head 254, 256 may comprise more than one light source 256 and/or more than one detector 254. The lights source(s) 256 may transmit light into the body tissue of the user 100, and the detector(s) 254 may receive the light travelled through the body tissue of the user 100. Alterations in the light received may be detected by the optical heart activity sensor and/or the processing circuitry, and thus, heart activity may be determined by the optical heart activity sensor and/or the processing circuitry, for example.

Let us now look closer on some embodiments of the wristband 200. Referring to FIG. 2A, the wristband 200 may comprise at least one pin 212 situated at the first portion 210 of the wristband 200. The at least one pin 212 may be configured to be placed into at least one opening 222 of the second portion 220 such that the first and second portion are physically attached to each other. As described earlier, the attachment may be detachable meaning that the at least one pin 212 may be removed from the at least one opening 222 in order to open the attachment and to remove the wrist device 102 from the wrist of the user 100, and/or, for example, to tighten or loosen the loop created by the wristband 200 around the wrist.

In an embodiment, two or more pins 212 are used to attach the first portion and the second portion together. This may make the attachment more reliable and/or firm. In an embodiment, the at least one opening 222 comprises a plurality of openings 222. The openings may be placed such that they enable progressive tightening and/or loosening of the wristband around the wrist. The wristbands may come in different lengths, for example. Thus, there may be small, medium and large wristband sizes in order to fit the wrist device 102 neatly around the wrist.

In an embodiment, the at least one pin 212 is made of metal and/or plastic. For example, iron may be used. In another example, plastic compound may be used.

Figure 3A:
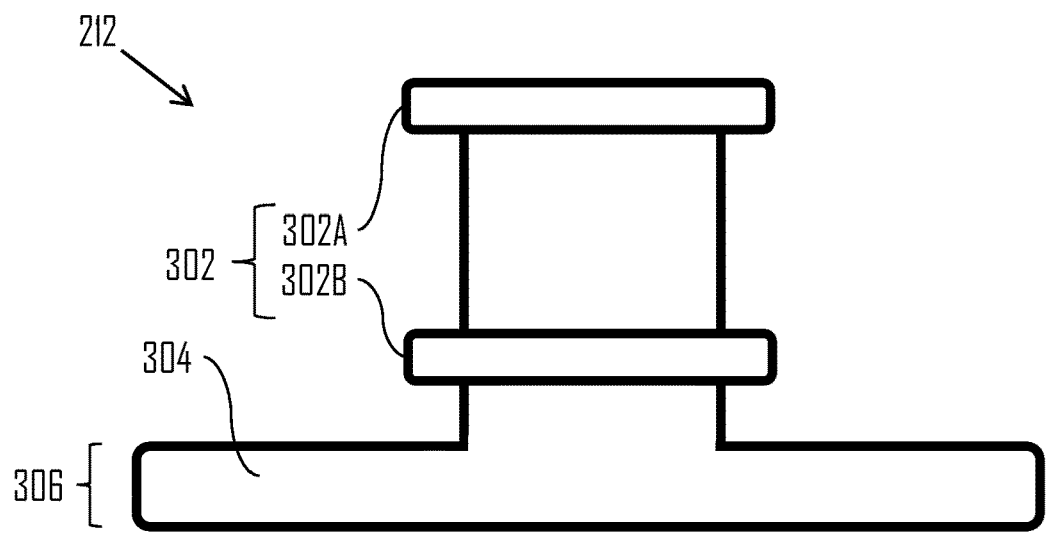
FIGS. 3A to 3E illustrate some embodiments.

In an embodiment, the at least one pin 212, as shown in an embodiment of FIG. 3A, comprises at least one bulge 302. As described earlier, the second portion may comprise the at least one opening 222 situated, wherein the at least one pin 212 is configured to at least partially penetrate the at least one opening 222, the at least one bulge 302 being adapted and dimensioned such that the at least one bulge 302 detachably locks the at least one pin 212 to the at least one opening 222. For example, the bulge 302 may penetrate through the second portion 220 of the wristband 200 through the opening 222. Outer dimensions of the bulge 302 may be greater than the inner dimensions of the opening 222, thus preventing the pin 212 from accidentally being removed from the opening 222. More particularly, the outer dimensions of a cross-section the part of the bulge 302 being placed against the second portion 220 may be greater than the inner dimensions of the opening 222.

The placement of the pin 212 and more specifically, the placement of the bulge 302 to the opening 222 may be enabled, at least partially, by the elastic structure of the wristband 200. The opening 222 may be enlarged when the pin 212 is being inserted into the opening 222, and the opening 222 may get back into its original form when the pin 212 is in the opening 222. Thus, the bulge 302 may be used to lock the pin 212 to the opening 222, and/or a mechanical force and/or friction force between the pin 212 and the opening 222 may prevent the pin 212 from being accidentally removed from the opening 222. Naturally, the user 100 may remove the pin 212 from the opening performing the placement of the pin 212 to the opening 222 in reverse order.

Such attachment mechanism for the optical heart rate measurement may be beneficial, as the tightness of the loop formed by the wristband may be progressively changed. Finding the right tightness for the wristband 200 may be beneficial for the efficiency and/or accuracy of the optical heart activity measurement as the placement of the optical heart activity circuitry against the wrist of the user 100 may need to be firm.

Figure 3B:
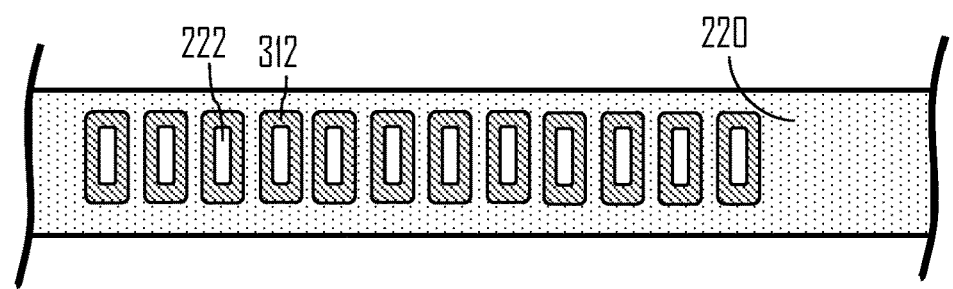

FIG. 3B illustrates an embodiment of the invention. Referring to FIG. 3B, the at least one opening 222 of the second portion 220 comprises a hollow 312 adapted and dimensioned to receive the at least one bulge 302 of the at least one pin 212. Each opening 222 may comprise one hollow. The hollow 312 may be dimensioned such that the outer dimensions of the bulge 302 are smaller than the inner dimensions of the hollow 312 and/or as great as the inner dimensions of the hollow 312. Thus, the bulge 302 may tightly fit to the hollow 312. The side of the second portion 220 on which the hollow is situated at may be the side to which the pin 212 penetrates through to. For example, the side may be the side that is configured to be placed against the wrist of the user. In the example of FIG. 2A, two sides of the wristband may be shown, wherein arrows 210A, 220A indicate the side of the first and second portions 210, 220 that are to be placed away from the wrist of the user 100, and wherein arrows 210B, 220B indicate the side of the first and second portions 210, 220 that is to be placed against the wrist. Therefore, the hollow 312 may be situated at the side 220B of the second portion 220, for example.

Similarly, the third portion may comprise A and B sides respectively although not shown in FIG. 2A.

In an embodiment, the first portion 210 is configured to be placed on the second portion 220 when the wristband 200 is in use. As seen in FIG. 2A, the first portion may be placed on the second portion 220 in order to insert the at least one pin 212 into the at least one opening 222. Thus, the first portion 210 may be at least partially against the second portion 220 and partially against body tissue of the user. The majority and/or the entire second portion 220 may be placed against body tissue of the user 100. Naturally this may mean that the side 220B may be placed against the body tissue. The side 210B of the first portion 210 may be placed at least partly against the side 220A of the second portion 220.

Referring to FIG. 3A, the at least one pin 212 may comprise a base plate 304. The base plate 304 may be adapted and dimensioned such that when the at least one pin 212 is attached to the first portion 210, the base plate 304 may be against the first portion 210.

In an embodiment, the at least one pin 212, when attached to the first portion 210, is substantially perpendicular in relation to the first portion 210. This may be seen in FIG. 2A, for example. In a way it may be understood that the at least one pin 212 extends outwards from a plane (e.g. the side 210B) provided by the first portion 210. In an embodiment, the at least one pin 212 is perpendicular to the side 210B of the first portion 210.

Looking at FIG. 2B, it may be seen that the wristband 200 may further comprise at least one opening 214 situated at the first portion 210 enabling a detachable attachment of the at least one pin 212 to the first portion 210. Thus, the at least one pin 212 may be arranged to be removed from the wristband 200 if needed. The attachment to the at least one opening 214 may be similar compared to the at least one opening 222 of the second portion.

In an embodiment, the at least one pin 212 is enabled to penetrate from a side of the first portion 210 to an opposite side of the first portion 210 through the at least one opening 214 of the first portion 210. The at least one opening 214 may comprise a hollow 216 adapted and dimensioned to receive the base plate 304 of the at least one pin 212 on said side of the first portion 210. For example, the at least one pin 212 may penetrate the at least one opening from the side 210A to the side 210B, as shown in the example of FIG. 2A. Thus, the hollow 216 may be situated at the side 210A, as shown in the example of FIG. 2B. Therefore, the part of the at least one pin 212 that is configured to be attached to the second portion 220 may be situated on the side 210B of the first portion 210.

In an embodiment, a depth of the hollow 216 is substantially same as a thickness of the base plate 304, wherein an area of a bottom of the hollow 216 is substantially the same as an area of the base plate 304 that is configured to be placed against the bottom of the hollow 216. The thickness of the base plate may be indicated with bracket 306 in FIG. 3A. Therefore, as the base plate 304 is arranged against the first portion 210, the base plate may be tightly fitted to the hollow 216. This may mean that the base plate 304 is embedded to the first portion 210 such that the base plate 304 does not substantially protrude outwards compared to the surface of the first portion 210. This may be seen in an embodiment of FIG. 3D, for example.

Referring to FIG. 3A, the at least one bulge 302 of the at least one pin 212 may comprise a first bulge 302A, the first bulge 302A adapted and dimensioned to detachably lock the at least one pin 212 to the at least one opening 222 of the second portion 220. The first bulge 302A may be situated at one head of the at least one pin 212, wherein the base plate 304 is situated in an opposite head of the at least one pin 212. This may be seen in FIG. 3A. Thus, when the pin 212 is inserted to the first portion, the pin 212 may be used to detachably attach the first portion 210 to the second portion 220 using at least one of mechanical force, friction force.

In an embodiment, the at least one bulge 302 further comprises a second bulge 320B, and the at least one opening 214 of the first portion 210 comprises a second hollow arranged on the opposite side (i.e. side 210B) of the first portion 210 compared to the side of a first hollow 216. The second bulge 302B may be enabled to penetrate the at least one opening 214 of the first portion 210, wherein the second hollow is adapted and dimensioned to receive the second bulge 302B, and wherein the at least one pin is enabled to be attached to the first portion 210 such that at least a part of the first portion 210 is situated between the base plate 304 and the second bulge 302B. Thus, the at least one pin 212 may be detachably attached to the first portion such that the second bulge 302B and the base plate 304 may keep the at least one pin 212 at its place. Naturally, the second bulge 302B may be dimensioned such that it may be bigger than the at least one opening 214. As described earlier, the elasticity of the wristband 200 may enable the opening 214 to be enlarged using physical force, and thus enable the pin 212 to be placed to the opening 214. When applying the physical force ends, the opening 214 may return to its original form. This may be applied to all the openings of the wristband 200.

Figure 3C:
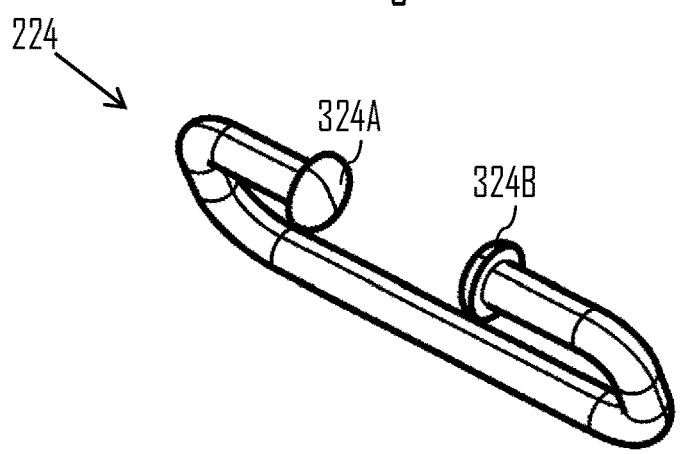
Figure 3D:
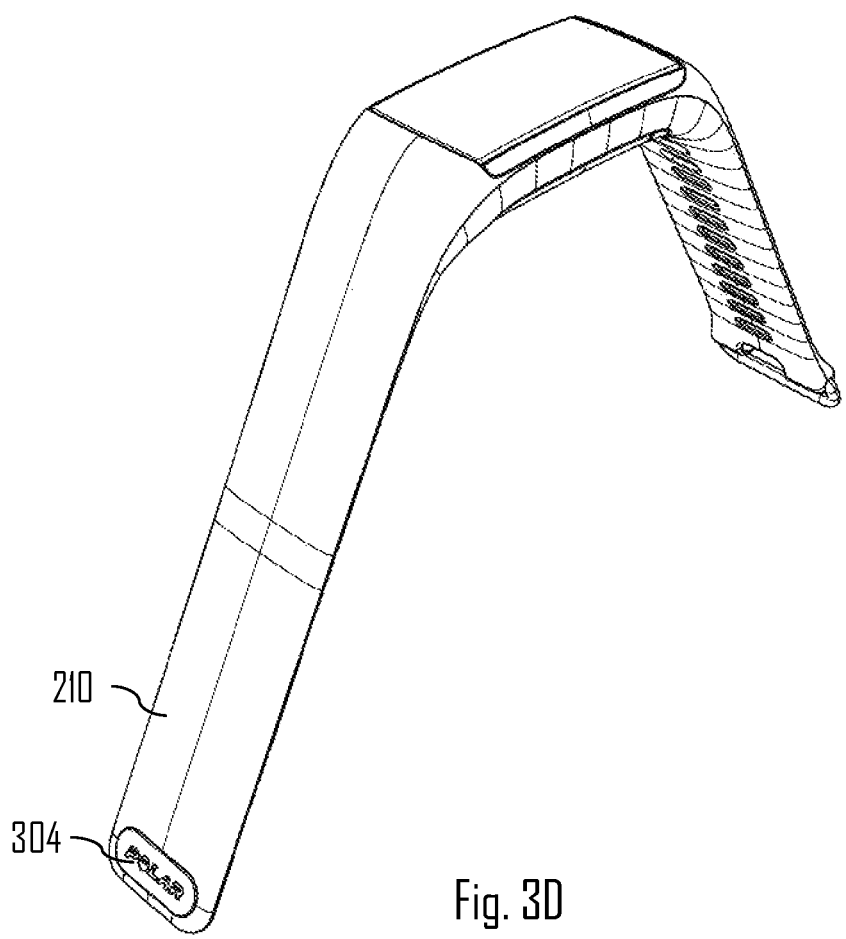

Referring to FIG. 2A, the second portion 220 may comprise a buckle 224 adapted and dimensioned such that the first portion 210 is, at least partially, enabled to slide through the buckle 224. The buckle 224 may be used as another contact means between the first and second portions 210, 220 together with the at least one pin 212. The buckle 224 may generate friction and/or mechanical force between the first and second portions 210, 220. This may enable the wristband 200 to be firmly attached against the wrist of the user 100. For example, the loop generated by the wristband 200 may be harder to accidentally loosen when the pin 212 and the buckle generate force to at least two different points of the loop. In an embodiment of FIG. 3C, the buckle 224 may be shown. The buckle 224 may be formed, for example, from a rod, wherein the ends 324A, 324B are bent to face each other as shown in FIG. 3C. The rod may be metallic and/or plastic, for example.

In an embodiment, the second portion 220 comprises a groove 226 situated at an end of the second portion 220, the groove being adapted and dimensioned to enable the at least one pin 212 to slide through the buckle 224. The groove 226 may enable the buckle 224 to be smaller as the hole generated between the buckle 224 and the end of the second portion 220 may be enlarged with the groove 226.

Figure 3E:
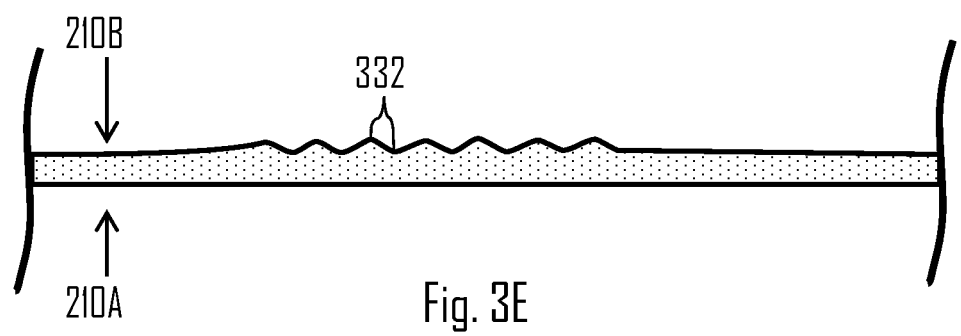

In an embodiment, the wristband 200 comprises friction elements causing friction between the first portion 210 and the second portion 220, when the first and second portions 210, 220 are connected to each other. For example, when the first and second portions 210, 220 are against each other when the wristband 200 is attached to the wrist, the friction elements may further decrease the chance to accidentally loosen the wristband 200. One example of said friction elements may be shown in an embodiment of FIG. 3E. In FIG. 3E, at least a portion of the second portion 210 may illustrated. The friction elements 332 may be situated at one side of the first portion 210. In the example, the friction elements 332 are situated at the side 210B that is to be placed against the second portion 220. The friction elements 332 may together with the buckle 224 generate force to decrease the chance of accidentally loosening the wristband 200. For example, at least one of the friction elements 332 may be placed against the end of the second portion 220 when the wristband 200 is in use. Thus, the end of the second portion 220 may be in one recess of the at least one of the friction element 332. This may further enhance the operation of the friction elements 332.

FIG. 2B may illustrate a situation, wherein the electronics module 250 is not within the holder 232. In FIG. 2A, the electronics module 250 may be mounted to the holder 232. In an embodiment, the holder 232 is adapted and dimensioned to at least partially surround the electronics module 250. This may be shown in FIG. 2A. Thus, the electronics module 250 may be at least partially protected by the holder 232 from external forces.

Looking closer on FIG. 2B, it may be seen that the holder 232 may comprise a through-hole. The through-hole may enable at least two different things. One may be to enable the displaying of information on the electronics module 250 (i.e. display of the electronics module 250). Second may be that the electronics module may be placed against the body tissue of the wrist, thus enabling the optical heart activity measurement by the electronics module 250.

In an embodiment, the display side of the holder 232 (e.g. side that may be facing outwards from the wrist) comprises transparent material. Thus, there may be no need to have a through-hole. The transparent material may be, for example, glass or plastic. The transparent material may enable the holder 232 to produce further supporting force to the electronics module 250, and thus make the optical heart activity measurement even more efficient. Actually, the transparent material may produce the force substantially towards the wrist which may be beneficial for the measurement.

In an embodiment, shown in FIG. 2B, the holder 232 comprises a first and second mounting elements 234A, 234B. The mounting elements 234A, 234B may be less elastic compared with the wristband 200. More precisely, the mounting elements 234A, 234B may be less elastic compared with the first, second and/or third portions 210, 220, 230. The mounting elements 234A, 234B may comprise, for example, hard plastic, such as Polyethylene Terephthalate (PET) and/or similar. The mounting elements 234A, 234B may enable firm attachment the electronics module 250 to the elastic wristband 200.

In an embodiment, at least one of the first and second mounting elements 234A, 234B comprises an alignment hollow 236 for an alignment element of the electronics module 250. The alignment hollow 236, as shown in FIG. 2B, may enable the electronics module 250 to be placed to the holder 232 in a correct and/or desired manner. The alignment hollow 236 may thus prevent misplacement and/or false attachment of the electronics module 250 to the wristband 200. As described, the electronics module may comprise the alignment element such that the alignment element is configured to be placed to the alignment hollow 236.

In an embodiment, the first and second mounting elements 234A, 234B are facing each other. This may be seen in FIG. 2B, for example. In an embodiment, the first and second mounting elements 234A, 234B are situated adjacent to each other on the wristband 200. This may mean that the mounting elements 234A, 234B are longitudinally adjacent to each other along the wristband 200.

In an embodiment, at least one of the first and second mounting elements 234A, 234B comprises a hollow for the electronics module 250. This may enable the electronics module 250 to be embedded at least partially in to the hollow.

In an embodiment, the first and second mounting elements 234A, 234B each comprise a claw enabling the mounting of the electronics module 250. The claws may lock the electronics module 250 into the holder 232. The electronics module 250 may comprise counterparts, such as hollows, fort the claws. Thus, the claws may be inserted to the hollows for the mounting to be more secure.

In an embodiment, the holder 232 comprises at least one hollow for receiving at least one button of the electronics module 250. The at least one button may be described later in more detail. However, the at least one button may comprise, for example, a mechanical button that may be used, for example, as multifunction button 251 of the electronics module 250. The at least one hollow in the holder 232 for the at least one button may be dimensioned such that the inner dimensions of the at least one hollow are substantially the same as the outer dimensions of the at least one button. Thus, the at least one button may be, for example, arranged into the at least one hollow relatively tightly. Further, the at least one hollow may be situated on the inner side of the holder 232 such that it may not be visible when the electronics module 250 is inserted to the holder 232.

In an embodiment, the holder 232 further comprises at least one protrusion arranged together with the at least one hollow, the at least one protrusion configured to enable mechanical energy transfer from the at least one protrusion to the at least one button of the electronics module 250. The at least one protrusion may enhance the usability of the at least one button. Thus, the at least one protrusion may indicate to the user 100, when the electronics module 250 is inserted into the holder 232, where the at least one button is located, and further enhance the using of the at least one button. The at least one protrusion may extend outwards from the holder 232. Thus, the at least one protrusion may be visible even though the electronics module 250 is fitted into the holder 232. Further, the at least one protrusion may be used with or without the at least one hollow. Thus, the at least one hollow may not necessarily be required, for example, to provide visual indication of the at least one button's location, when the electronics module 250 is mounted to the holder 232.

In an embodiment, the at least one opening 222 of the second portion 220 comprises a hollow adapted and dimensioned to receive the at least one bulge 302.

Figure 4A:
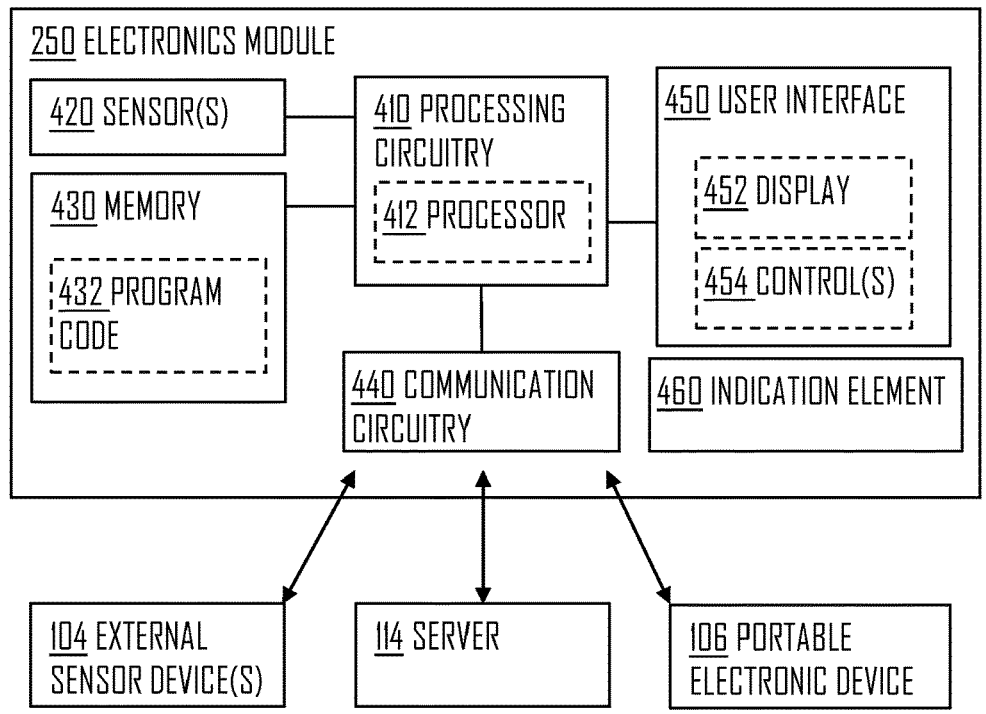
FIGS. 4A to 4B illustrate some embodiments.
Figure 4B:
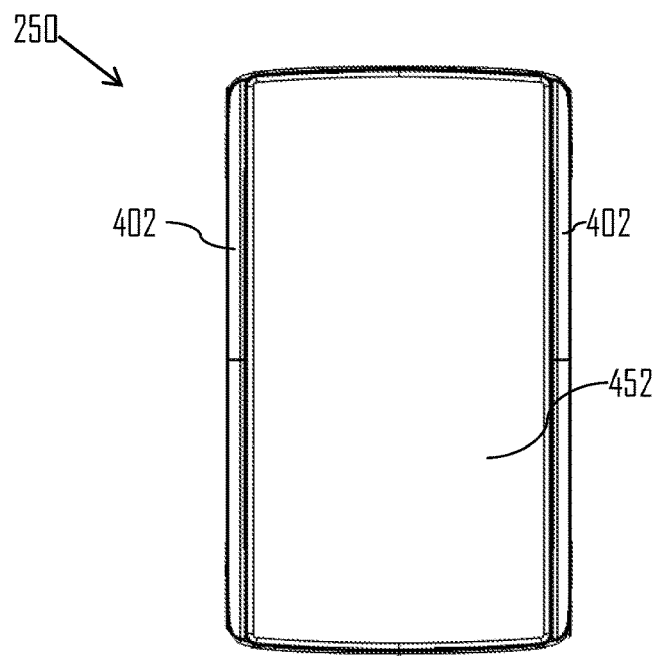

Let us now look closer on some embodiments of the electronics module 250. FIGS. 4A to 4B illustrate some embodiments of the invention. Referring to FIG. 4A, the electronics module 250 may comprise a communication circuitry 440 configured to enable communication with an external device, such as the external sensor device(s), server 114 and/or the portable electronic device 106. The communication circuitry 440 may be a wireless communication circuitry, for example. The communication circuitry 440 may be based on Bluetooth® specifications, i.e. Bluetooth Low Energy, and/or Near-Field-Communication (NFC) technology, wherein the NFC technology may enable data transfer on short distances. However, the wireless communication circuitry 440 may not be limited to these technologies, and thus it may support, for example, cellular connection (i.e. 2G, 3G, LTE, LTE-A, 4G, 5G), and/or Wireless Local Area Network (WLAN) connection. Further, for example, ANT+ may be supported by the communication circuitry 440.

Referring to FIG. 4B, the electronics module 250 may further comprise an antenna structure 402 electrically coupled with the communication circuitry 440. The antenna structure 402 may be configured to radiate according to received and/or transmitted electromagnetic energy. The antenna structure 402 may, for example, be situated on at least one edge area of the electronics module 250, as shown in FIG. 4B.

In an embodiment, the communication circuitry 440 comprises a Bluetooth circuitry, wherein the antenna structure 402 comprises a Bluetooth antenna.

In an embodiment, the electronics module 250 comprises a cable port configured to receive an external cable, wherein the cable port enables a charging a battery of the electronics module 250, and/or transferring data between the electronics module 250 and the external device. As shown in FIG. 2C, the cable port may be covered by a protective cover 258. This may, for example, prevent dirt from going to the cable port. For example, if the cable port is against the body tissue of the user 100, the skin of the user 100 may gradually get stuck within the cable port and possibly jeopardize usage of the cable port for data and/or energy transfer. The cable port may be and/or comprise, for example, Universal Serial Bus (USB) port.

In an embodiment, the electronics module 250 comprises an input interface configured to enable wireless charging of the electronics module 250. The input interface may be configured to receive magnetic flux, and to convert the magnetic flux into electricity in order to load the battery of the electronics module 250.

The modular structure of the wrist device 102 may, for example, enable the electronics module 250 to be detached from the wristband 200. This may further allow the electronics module to be recharged when the wristband 200 is still on. This may be beneficial, for example, if the wrist device 102 is not wanted to be removed from the wrist. Further, more than one electronics module may be used, and thus the electronics module may be switched to another when it is recharged. As described, the recharging may be wireless and/or wired.

Referring to FIG. 4A, the electronics module 250 may comprise a user interface 450 configured to enable the user to interact with the electronics module 250. The user interface may comprise a display 452 and/or control(s) 454. The display 452 may capacitive or resistive touch-screen display, for example. It may also be a non-touch display meaning that it may not necessarily comprise control(s). In an embodiment, the display 452 comprises a sapphire glass. In an embodiment, the display 452 comprises a touch-screen display.

In an embodiment, shown in FIG. 4B, the antenna structure 402 is comprised in at least one edge area of the display 452. For example, at least some surroundings of the display 452 may comprise the antenna structure 402. Placing the antenna structure 402 as described may enhance the function of the antenna structure 402 as the radiated electromagnetic energy may be less interfered by the wrist of the user 100, for example. This may be due to the fact that the antenna structure 402 may be facing a direction opposite compared to the direction of the wrist.

Still referring to FIG. 4A, the electronics module 250 may comprise the processing circuitry 410, as explained above. The processing circuitry 410 may comprise at least one processor 412. In an embodiment, the at least one processor is comprised in the electronics module 250. The electronics module 250 may further comprise at least one memory 430, wherein the at least one memory 430 may comprise a computer program code 432. The at least one memory 430 and the computer program code 432 may be configured, with the at least one processor 412, to perform any of the functions of the electronics module 250. This may mean that the functions are either performed by the at least one memory 430 and the computer program code 432, with the at least one processor 412, and/or that said entity causes some other element, such as the communication circuitry 440, to perform some function.

In an embodiment, the processing circuitry 410 comprise the at least one processor 412 and the at least one memory 430.

Further, the electronics module 250 may comprise at least one sensor 420. For example, the optical heart activity circuitry may be comprised in the electronics module, as described. Further sensors that were described to be comprised in the wrist device 102 may be comprised in the electronics module 250. For example, the at least one sensor 420 may comprise motion sensor and/or GPS sensor.

In an embodiment, the electronics module 250 comprises a motion circuitry configured to measure motion of the user 100, wherein the processing circuitry 410 is further configured to obtain the motion measurement data, and to process said data into a motion metric characterizing a motion of the user 100. The motion circuitry may be comprised in the sensor(s) 420, for example.

In an embodiment, the electronics module 250 comprises an indication element 460 configured to indicate an event to the user of the electronics module 250 using a haptic indication, sound indication and/or visual indication. The event may be, for example, incoming phone call and/or physical training related event, such as exceeding of a heart rate zone limit.

Figures 5, 6A:
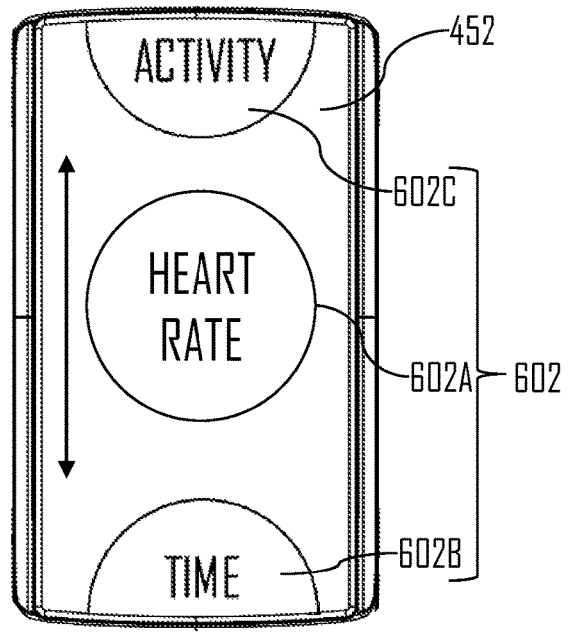
FIG. 5 illustrates an embodiment of the invention.
FIGS. 6A to 6B illustrate some embodiments.

In an embodiment, as shown in step 510 of FIG. 5, the processing circuitry 410 is configured to determine that the electronics module 250 is not used for a predetermined time. For example, the processing circuitry 410 may determine that no user input to the display 452 and/or to the control(s) 454 is detected. Further, for example, the at least one sensor 420 may be used to determine if the electronics module 250 used (i.e. heart beat detection, motion detection). In step 520, based on the determination, the electronics module 250 may dim the display 452 and/or turn off the display 452.

Figure 6B:
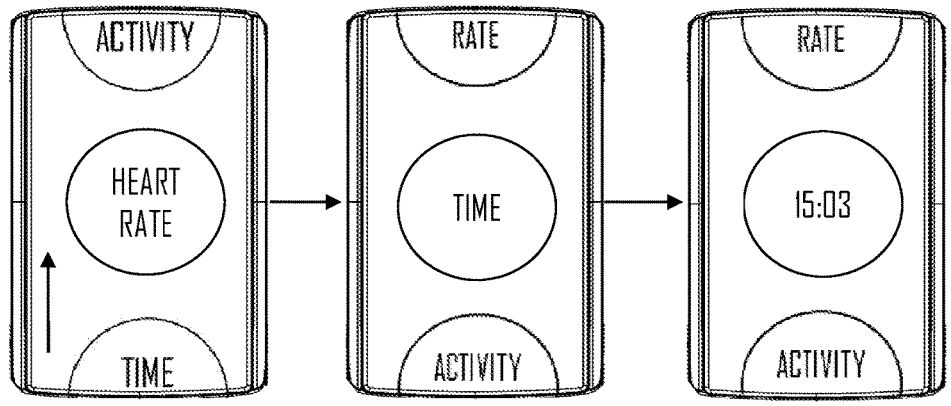

FIGS. 6A to 6B illustrate some embodiments. Referring to FIG. 6A, the display 452 may be configured to display at least one menu element 602A of a plurality of menu elements 602, wherein the displayed at least one menu element is enabled to be changed by scrolling the display 452. For example, if the display 452 is a touch-screen display, swiping the display may enable the switching of the displayed menu element 602. It may be beneficial to also show at least some of the other menu elements 602B, 602C because the user 100 may then be aware what menu element 602 is selected next if the display is scrolled.

In an embodiment, the plurality of menu elements 602 is enabled to be scrolled in an endless loop. For example, three menu elements (i.e. 1, 2, 3) may be scrolled to one direction (i.e. up, down, left, right) such that first number 1 is displayed, then number 2, then number 3, then again number 1, and so on.

In an embodiment, the menu elements 602 are enable to be scrolled up and/or down, as indicated by an arrow in FIG. 6A.

Referring to FIG. 6B, the plurality of menu elements 602 comprises a time menu element, wherein the processing circuitry 410 is configured to detect that the time menu element is selected by scrolling the display 452, and to cause the display 452 to automatically display time when the time menu element is selected. This may be seen in the example of FIG. 6B, wherein first heat rate is displayed. Then the user 100 scrolls the display as indicated by the arrow, which causes the selection of the time menu element. Further, the display 452 may then automatically display time after the selection is detected by the processing circuitry 410. Similarly, any other menu element 602 selection may be detected and caused to be displayed automatically. For example, if the user 100 selects the heart rate menu element, the electronics module 250 may automatically start to display the heart rate if it is available.

In an embodiment, the selection of the menu elements 602 requires a user input, such as pressing of the control(s) 454 and/or touch-screen press.

In an embodiment, the user interface 450 comprises at least one button.

In an embodiment, the at least one button comprises a multifunction button, and wherein pressing the multifunction button causes at least one of the following: switching the electronics module on, switching the electronics module off, pairing the electronics module with the external device, changing of a current display element to a previous display element, stopping a physical activity recoding.

In an embodiment, the multifunction button is a mechanical button.

In an embodiment, the body 252 of the electronics module 250 comprises a first and a second mounting counterparts corresponding to a first and a second mounting elements of the holder 232 of the wristband 200.

In an embodiment, the first and second mounting counterparts each comprise a hollow corresponding to claws of the first and second mounting elements 234A, 234B of the holder 232 of the wristband 200. For example, the first and second mounting counterparts may be hollows for the claws.

In an embodiment, the body 252 comprises at least one groove enabling embedding the electronics module 250 to the holder 232 of the wristband 200.

In an embodiment, the body 252 comprises an alignment element corresponding to an alignment hollow of the holder 232 of the wristband 200, the alignment element enabling and/or enhancing alignment of the electronics module 250 to the holder 232. For example, the alignment element may be a rod which may be used to align the electronics module 250 to the holder 232 by aligning the rod with the alignment hollow.

Figure 7A:
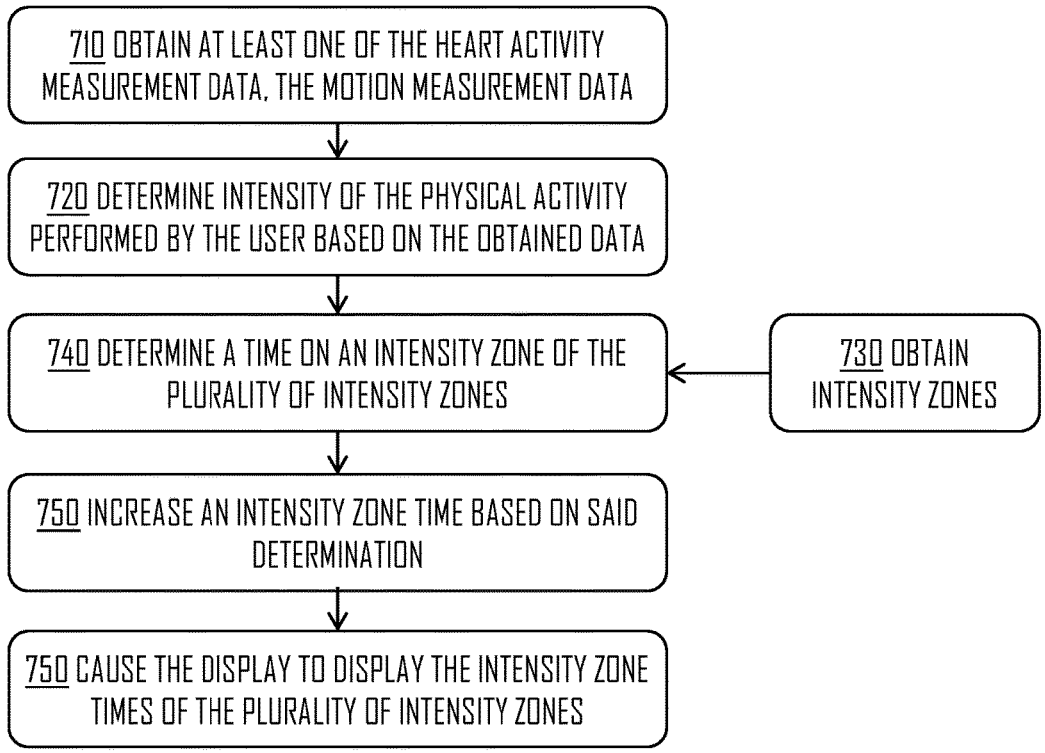
FIG. 7A illustrates a block diagram according to an embodiment.

FIGS. 7A to 7B illustrate some embodiments of the invention. Referring to FIG. 7A, the processing circuitry 410 may be configured to obtain at least one of the heart activity measurement data, the motion measurement data (step 710), and to determine intensity of the physical activity performed by the user 100 based on the obtained data (step 720). For example, the intensity may refer to calorie burn rate and/or to heart rate.

In step 730, the processing circuitry 410 may obtain a plurality of intensity zones. For example, the intensity zones may comprise zones from 1 to 5, wherein the zone 1 may be the least exhaustive and the 5 may be the most exhaustive zone.

In step 750, based on the intensity of the physical activity (step 720), the processing circuitry 410 may determine a time on an intensity zone of the plurality of intensity zones, and in step 760, increase an intensity zone time based on said determination of step 750.

In step 770, the processing circuitry 410 may be further configured to cause the display 452 to display the intensity zone times of the plurality of intensity zones. An example of this may be seen in FIG. 7B. In the example, time on the intensity zones from 1 to 5 may be displayed together with training time, current calorie consumption and current heart rate. The time on the intensity zones may be, for example, displayed using bars. The bars may be color coded, for example.

FIG. 8 illustrates an embodiment of the invention. Referring to FIG. 8, the processing circuitry 410 may be configured to detect at least one gesture performed by the user (step 810), and based on the detected at least one gesture, to cause a function to be performed on the electronics module 250 (step 820). The gesture may be detected by the sensor(s) 420, such as an accelerometer and/or gyroscope of the motion circuitry.

In an embodiment, the electronics module 250 comprises a camera configured to detect at least one facial feature of the user 100. This may also trigger the action described earlier.

The gesture(s) may comprise, for example, detecting that the user 100 looks at the electronics module 250 and/or the display 452. This may be detected, for example, by using the motion circuitry to detect that the user lifts and rotates the arm to which the wrist device 102 is attached to. Further, the camera may be used to detect the same gesture.

In an embodiment, the function comprises displaying the heart activity metric on the display. For example, when the user lifts and rotates his/her arm, the display 452 may be caused to display the heart activity metric, such as heart rate of the user 100.

In an embodiment, the function comprises at least one of the functions of the multifunction button.

In an embodiment, the function comprises scrolling the display 452 of the electronics module 250. For example, the plurality of menu elements 602 may be scrolled by rotating the wrist device 102 when the wrist device 102 is worn by the user 100. For example, the direction of the rotation may be used to control the scrolling to up and/or down directions.

In an embodiment, the processing circuitry 410 first detects that the wrist device 102 is looked at by the user 100. As described, this may be detected using the motion circuitry and/or camera, for example. Second, after the detection, the processing circuitry 410 enables the display 452 to be scrolled by rotating the wrist device 102. This may, for example, reduce the amount of accidental scrolls, thus saving battery of the device.

In an embodiment, the processing circuitry 410 is configured to determine that the user is exercising, detect the at least one gesture, and cause the display 452 to display the heart activity metric. This may mean that before the heart activity metric is displayed using the gesture detection, it first needs to be determined that the user 100 is exercising. This determination may be based on, for example, heart activity, motion activity, intensity zone information, user input, to name a few examples. For example, the user 100 may tell the device 102 that he/she is starting a running exercise, and thus the gesture detection may be enabled. The exercise may comprise, for example, running, bike riding, climbing, playing a team sport, skiing, to name a few examples.

FIG. 9 illustrates an embodiment of the invention. Referring to FIG. 9, in step 910, the electronics module 250 may determine that at least one external sensor, such as the external sensor device(s) 104, is coupled with the electronics module 250. In step 920, the electronics module 250 may process at least one of the heart activity metric, the motion metric based at least partly on data from the at least one external sensor. For example, if an external heart rate transmitter (i.e. chest, arm belt, ear sensor) is worn by the user 100, the electronics module 250 may receive heart activity measurement data from the external heart rate transmitter. The electronics module 250, or more precisely the processing circuitry 410, may use the received data and/or data from the internal optical heart activity circuitry to determine user's 100 heart activity. It needs to be further noted that the same analogy may be used for motion sensor(s), such as a cadence sensor worn on the foot and/or on a pedal, acceleration sensors, GPS, to name a few examples.

In an embodiment, the electronics module 250 determines that the external heart rate transmitter is worn by the user 100. In response to the determining, the electronics module 250 uses only the heart activity measurement data from the external heart rate transmitter in order to determine user's heart activity. In one example, the optical heart activity circuitry may be used first for the heart activity determination. Then the external heart activity transmitter may be connected, and in a response, the data from the external heart activity transmitter may be used for the heart activity determination instead of the data from the optical heart activity circuitry. For example, it may be beneficial to use external sensor(s) in order to save battery of the electronics module 250.

In an embodiment, the user 100 is prompted which sensor data he/she wants to use. For example, the user 100 may want to use optical heart activity circuitry data when he/she is running. However, when he/she starts to ride a bicycle, it may be beneficial to use the data from the external heart rate transmitter, for example.

In an embodiment, the electronics module 250 determines the sport and/or activity that the user 100 is currently performing. Based on the determination and user preferences, the data source for the heart activity determination may be selected. For example, the user 100 may have selected that for running he/she wants to use optical heart activity circuitry, and for riding the bicycle the external heart activity transmitter may be preferred. The electronics module 250 may determine the activity based on the information from the sensor(s) 420, from user input and/or from external sensor device(s) 104. Further, if, for example, the first user preference is not detected (i.e. external heart activity transmitter is not detected) the second preference and/or second possible source may be used. This may happen automatically, for example.

Figure 11:
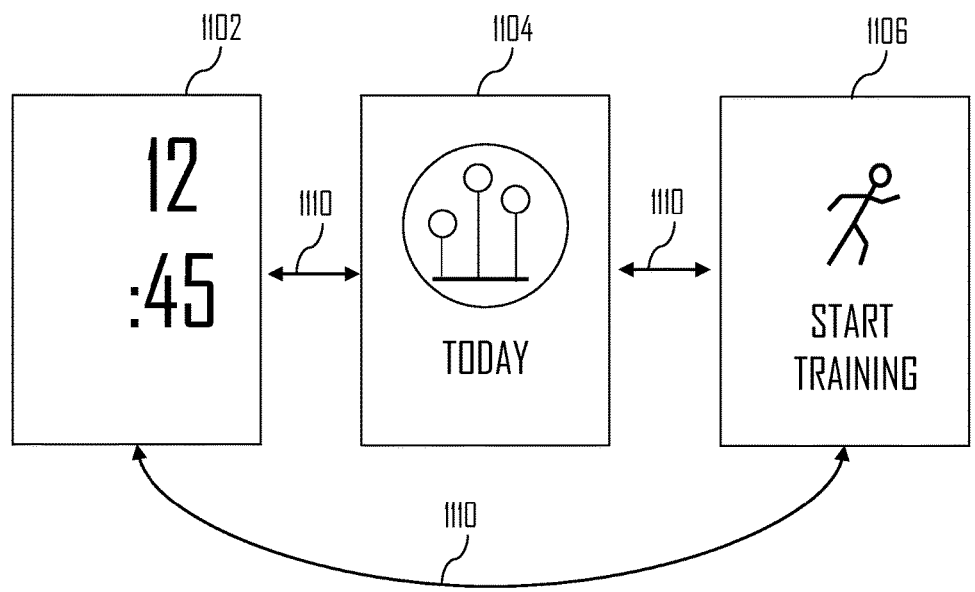
FIG. 11 illustrates an embodiment.

FIG. 11 shows an embodiment of the invention. Referring to FIG. 11, menu elements 1102, 1104, 1106 may be shown. The menu elements 1102, 1104, 1106 may be similar and/or identical with the menu elements 602. For example, the time menu element 602C may be similar and/or identical to a time menu element 1102 (i.e. indicating time), for example. Arrows 1110 indicate, as explained above, that the menu elements 1102, 1104, 1106 may be scrolled, for example, on the display 452 (i.e. touch display). The menu elements 1102, 1104, 1106 may be scrolled in a loop, for example. The scrolling may happen laterally and/or vertically on the display 452. One example of vertical scrolling may be shown in FIG. 6A. As explained, the scrolling may be performed, for example, by swiping finger for a certain length on the display. The electronics module 250 may determine the direction of the swipe, and display the next menu element according to the direction of the swipe. A menu element among the menu elements 1102, 1104, 1106, may be selected, for example, by tapping the display 452. The tapping may be detected by the electronics module 250, and at least some content of the selected menu element may be shown on the display. For example, sub-menu element(s), related to the selected menu element, may be shown.

In an embodiment, the electronics module 250 determines that a touch of the display 452 is a tap, if the touching lasts under 200 milliseconds (ms). In an embodiment, the touch is determined to be a tap if it lasts between 1 ms to 100 ms. In an embodiment, the touch is determined to be a tap if it lasts between 1 ms to 200 ms.

Looking closer on different menu elements, such as the menu elements 1102, 1104, 1106, the menu element 1104 may indicate a timeline menu element 1104. The timeline menu element 1104 may comprise content which relates to activity of the user 100 during the ongoing day, for example. Naturally different time periods, such as a hour, a week and/or a month, to name a few, may also be possible to be shown when the timeline menu element 1104 is selected. The timeline menu element 1104 is further discussed with reference to FIGS. 10A to 10H.

In an embodiment, the electronics module 250 determines activity of the user 100 during a predetermined time, and displays at least some of the determined activity on the display 452. For example, the predetermined time may be the ongoing day, and thus the activities may comprise past and/or future activities. The determined activity may be displayed in a timeline view that may be opened from the timeline menu element 1104.

Figure 10A:
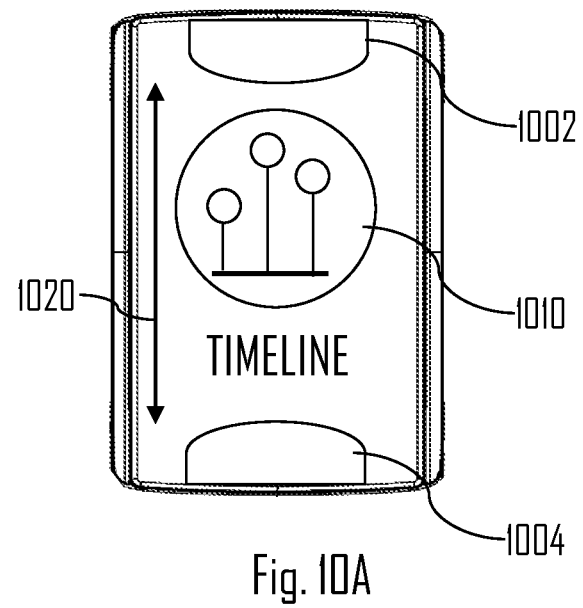
FIGS. 10A to 10H illustrate some embodiments.

Referring to FIG. 10A, menu elements 1002, 1004, 1010 may be at least partially shown, and scrolled on the display 452 as indicated by the arrow 1020. For example, one or more of the menu elements 1002, 1004, 1010 may be shown at a time on the display 452. The menu elements 1002, 1004, 1010 may be similar and/or identical to menu elements 602 and/or menu elements 1102, 1104, 1106. For example, the timeline menu element 1010 may be similar to timeline menu element 1104 shown in FIG. 11.

Figure 10B:
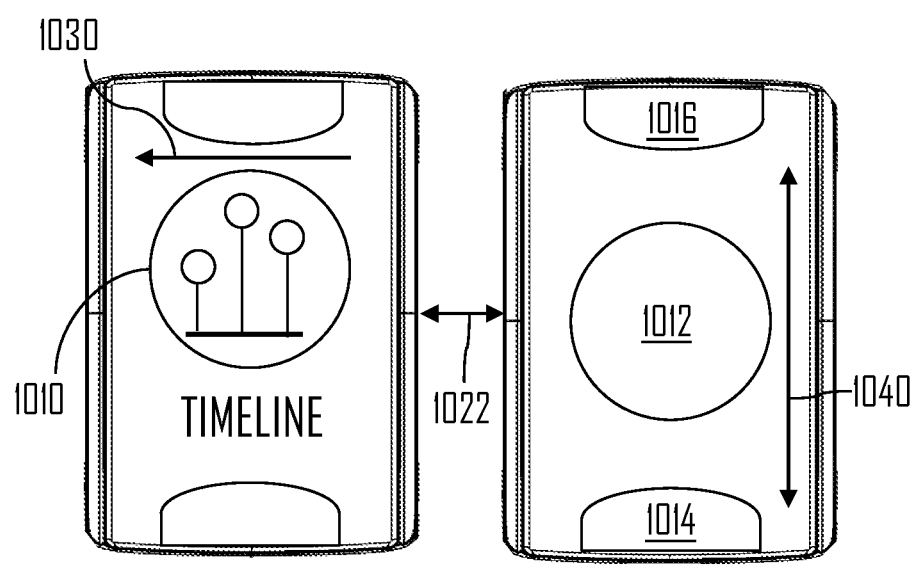
Figure 10C:
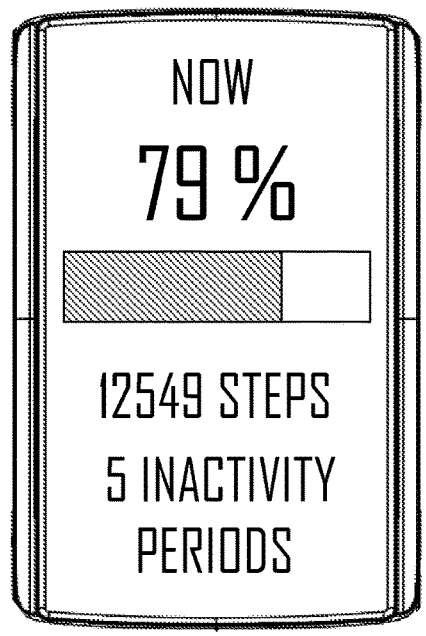

Referring to FIG. 10B, a menu element, such as the timeline menu element 1010, may be selected by tapping the menu element 1010, tapping the display 452 when the display shows the menu element that is wanted to be selected and/or the user 100 may select the shown menu element by swiping the screen, for example, laterally. For example, if the menu elements 1002, 1004, 1010 may be scrolled vertically (e.g. from top to bottom and/or vice versa) on the display 452, the selecting may happen by swiping the display 452 laterally (e.g. from right to left and/or from left to right). The swiping is indicated with an arrow 1030 in FIG. 10B.

An arrow 1022 may indicate that when the menu element, such as the timeline menu element 1010, is selected, another view may be displayed on the display 452. Naturally, said another view may be related to the selected menu element 1010, and thus, said another view may be, for example, a sub-menu of the menu element 1010, wherein the sub-menu comprises one or more sub-menu elements 1012, 1014, 1016. By swiping the display 452 to an opposite direction compared to the direction of the selection swiping indicated with the arrow 1030, may cause the electronics module 250 to cause the display 452 to show at least one of the menu elements 1010, 1002, 1004. For example, if the sub-menu was related to the timeline menu element 1010, the opposite direction swiping may cause the display 452 to display the timeline menu element 1010 (i.e. act as a back function). As shown with an arrow 1040, the sub-menu elements 1012, 1014, 1016 may be scrolled on the display 452. The scrolling and/or displaying of the sub-menu elements 1012, 1014, 1016 may be similar to that of scrolling and/or displaying of the menu elements 1010, 1002, 1004, for example. Also, the at least one button may be used as a back button enabling the electronics module 250 to cause the display 452 to display the previous view when the at least one button is pressed.

In FIGS. 10C to 10H, sub-views and/or sub-menu elements of a timeline view may be shown. The timeline view may be opened by selecting the timeline menu element 1010, for example. Similarly, there may be views comprising sub-views for each of the menu elements 1010, 1002, 1004.

As described, the sub-menu elements and/or sub-views may be enabled to be displayed once the corresponding menu element is selected. One or more sub-menu elements and/or sub-views may be displayed at a time.

Figure 10D:
Figure 10E:
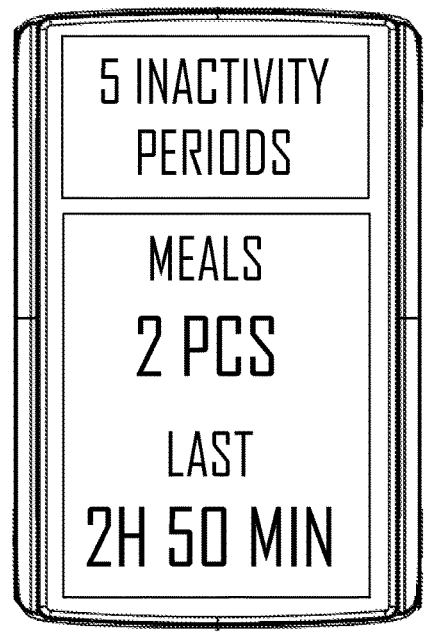
Figure 10F:
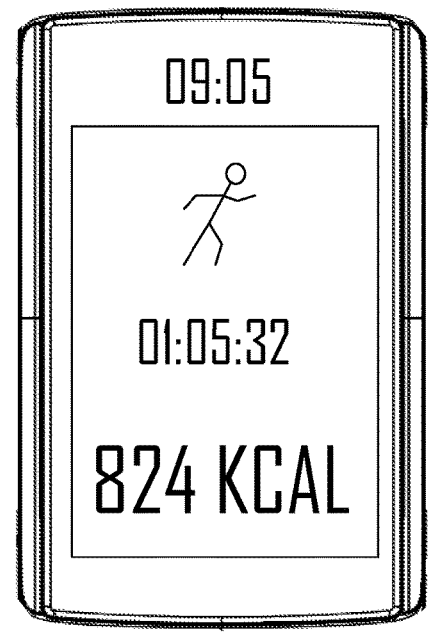
Figure 10G:
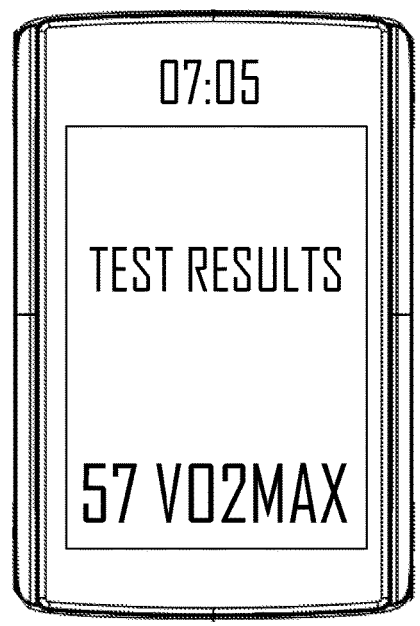
Figure 10H:

Each Figure of the FIGS. 10O to 10H may illustrate one sub-view and/or sub-menu element shown when the timeline menu element 1010 has been selected. Thus, the sub-views of FIGS. 10O to 10H may be comprised in the timeline view that may be opened by selecting the timeline menu element 1010.

It needs to be noted that views, opened by selecting at least one of the menu elements 1002, 1004, 1010, for example, may each comprise different sub-menu elements and/or sub-views related to the topic of the selected menu element. Thus, for example, referring to FIG. 10O, the timeline view may comprise a sub-view indicating physical activity of the user 100 during some period, such as during the ongoing day. Thus, for example, number of steps taken during the day may be displayed. Similarly, number of inactivity periods may be displayed. It may also be possible to use a percentage and/or graph to indicate how much of the daily activity goal has been reached.

Referring to FIG. 10D, another sub-view of the timeline view may be shown. Said another sub-view may indicate planned exercise(s) for the timeline period, wherein the period may be, for example, the ongoing day. The electronics module 250 may be configured to enable scrolling of the planned exercises if there is more than one exercise planned.

Referring to FIG. 10E, another sub-view of the timeline view may be shown. Said another sub-view may indicate meal information of the user 100. For example, the meal information may comprise meals eaten, time from the last meal, and/or time when each meal was eaten. Further, the number of inactivity periods may be displayed. Again, the timeline period may be, for example, the ongoing day and thus, the meal information of the ongoing day may be displayed.

Referring to FIG. 10F, Referring to FIG. 10E, another sub-view of the timeline view may be shown. Said another sub-view may indicate information related to performed exercises of the user 100. For example, information related to the performed exercises during the ongoing day may be shown. The information related to the performed exercises may comprise burned calories during the performed exercises and/or total time spent on exercising, for example.

Referring to FIG. 10G, another sub-view of the timeline view may be shown. Said another sub-view may indicate information related to fitness test results, for example. One example of such may be a VO2MAX result. The information shown may be related to last taken fitness test(s) and/or to fitness test(s) that have been performed during the timeline period.

Referring to FIG. 10H, another sub-view of the timeline view may be shown. Said another sub-view may indicate information related to sleeping of the user 100. For example, duration of sleep during the timeline period may be shown. The electronics module 250 may determine that the user 100 needs more sleep (e.g. the user 100 has sleep deprivation). The determination may be based on recorded sleep time, quality of sleep, performed exercises and/or planned exercises, for example. Thus, the information related to sleeping may comprise instructions to take a nap and/or recommendation for a minimum time to sleep and/or rest.

In an embodiment, the timeline menu element 1010 is selectable after the electronics module 250 has detected physical activity by the user 100. For example, the physical activity may comprise a recorded exercise, recorded meal and/or recorded sleep. Similarly, the sub-view may be activated when there is information to be shown in the sub-view. For example, if there are no planned exercises for the ongoing day, the sub-view indicating the planned exercises may be inactive (e.g. no shown). If the user 100 inputs a planned exercise for the ongoing day, the sub-view may be activated. Similarly, if there exists recorded information about performed exercises, the sub-view indicating the performed exercises may be activated.

Figure 12A:
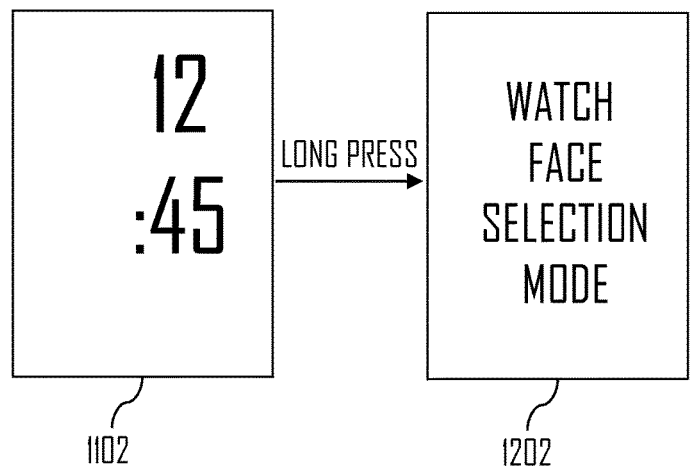
FIGS. 12A to 12C illustrate some embodiments.
Figure 12B:
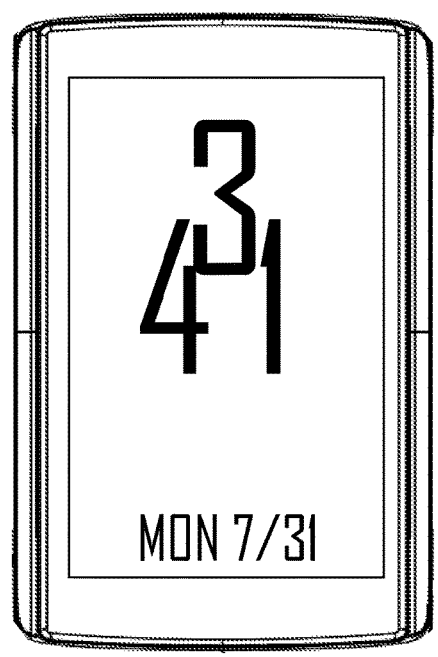
Figure 12C:
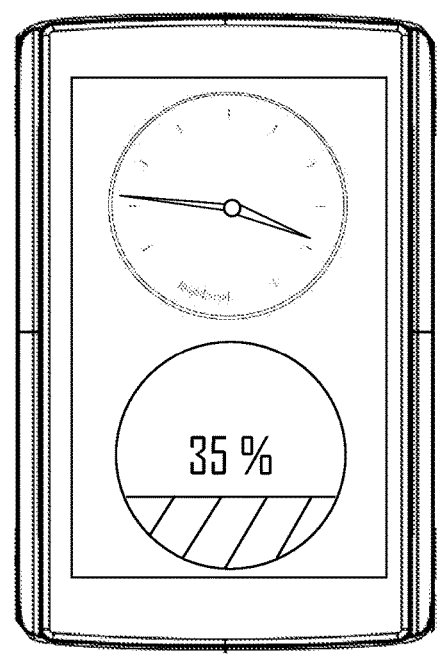

FIGS. 12A to 12C illustrate some embodiments. Referring to FIG. 12A, the electronics module 250 may be configured to cause on the display 452 to display the time menu element 1102. The electronics module 250 may detect that a user presses and/or selects the time menu element 1102, and cause the display 452 to display and/or activate a watch selection mode 1202. In an embodiment, the watch selection mode 1202 is activated when the display 452 is pressed for and/or over a predetermined time. The predetermined time may be longer compared to a time required to press the display 452 when selecting a menu element, such as for example, the timeline menu element 1010. In an embodiment, the watch selection mode 1202 is activated when the display 452 is pressed for and/or over the predetermined time when the display 452 is displaying the time menu element 1102.

In an embodiment, said predetermined time is 2 seconds. The predetermined time may be, for example, 0.5 seconds, 1 second, 3 second and/or 5 seconds, to name a few examples.

For example, the user 100 may select the time menu element 1102, which may cause the electronics module 250 to display alarm clock configuration. When the user presses the time menu element 1102 for said predetermined time, the watch face selection mode 1202 may be activated. Thus, the time the display 452 is pressed may cause the electronics module 250 to perform a different action depending on the detected duration of the press.

FIGS. 12B and 12C may indicate different watch faces of the watch face selection mode 1202. For example, the user 100 may scroll the different watch faces on the display 452, and select the wanted watch face. Selection may be performed by, for example, tapping the display 452. The selected watch face may be displayed on the display 452 as the time menu element 1102, for example. Thus, the user may choose what kind of watch face is displayed as the time menu element 1102.

Referring to FIG. 12C, the shown watch face may comprise virtual clock hand(s) indicating time. In an embodiment, the watch face comprises a percentage and/or graph of achieved daily activity goal.

Figure 13:
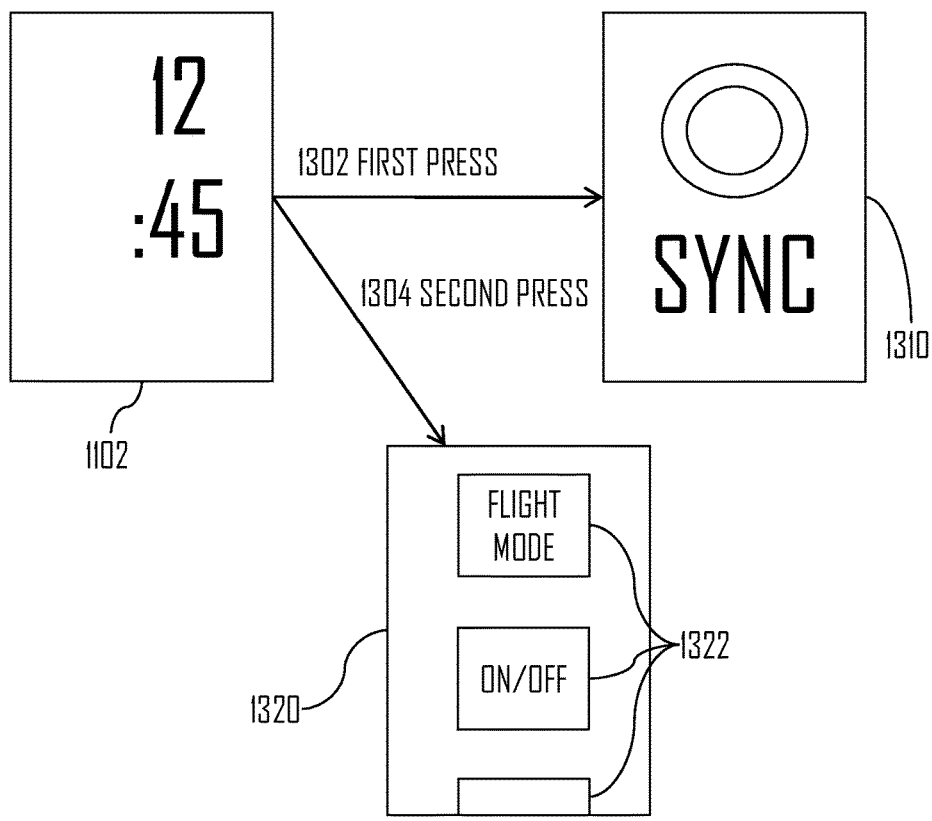
FIG. 13 illustrates an embodiment.

FIG. 13 illustrates an embodiment of the invention. As described above, the electronics module 250 and/or the user interface 450 may comprise the at least one button, such as a multifunction button. The at least one button may be comprised in the control(s) 454 that is comprised in the user interface 450, for example. Referring to FIG. 13, the electronics module 250 may detect a duration the at least one button is pressed by the user 100. For example, a first press 1302 and/or a second press 1304 may be detected, wherein the second press 1304 is longer compared to the first press 1302. In an embodiment, the first press 1302 is at least 2 seconds and the second press 1304 is at least 4 seconds. Thus, for example, if the electronics module 250 detects that the at least one button is pressed for duration of two seconds but less than 4 seconds, the electronics module may determine that the first press 1302 is detected.

The detected first press 1302 may cause the electronics module 250 to activate the communication circuitry 440 and/or to cause the communication circuitry 440 to activate synchronization with an external device. The synchronization may be also referred to as pairing, as described above. For example, Bluetooth (i.e. BLE) scanning may be activated. During the synchronization, a synchronization display element 1310 may be displayed on the display 452. If the at least one button is pressed during the synchronization, the synchronization may be paused and/or stopped. Further, the electronics module 250 may then cause the display 452 to display the previous display element, such as the time menu element 1102.

The detected second press 1304 may cause the electronics module 250 to access a system menu 1320 of the electronics module 250. The system menu 1320 may comprise one or more menu elements 1322. The one or more menu elements 1322 may comprise flight mode selection, on/off-switch and/or system information part. The menu elements 1322 may be scrolled and/or selected by the user 100 on the display 452.

In an embodiment, the electronics module 250 detects that the user selects the system menu 1320. The electronics module 250 may then detect a user input, and based on the user input, cause the electronics module 250 to go in flight mode, turn off, or to display system information. The flight mode may mean that communication circuitry 440, such as Bluetooth, is turned off. Thus, the electronics module 250 may not transmit and/or receive wireless signals when in flight mode.

In an embodiment, the electronics module 250 detects the duration that the at least one button is pressed. Based on the duration, the electronics module 250 may determine whether the press is the first press 1302, the second press 1304, or a third press. The third press may equal to a back press, meaning that the detected third press may cause the electronics module 250 to display previous view on the display 452. The first press 1302 may be detected if the press lasts 0.5 s-1 s, or 0.5 s-2 s, for example. The second press 1304 may be detected if the press lasts over 1 s, or over 2 s, for example. Thus, the third press may be detected if the press last for under 0.5 s or under 1 s. The times required for different press detections may be arranged such that they may not overlap with each other. In an embodiment, the times required for different press detections at least partially overlap with each other. Further, duration of the first press 1302 may be less than duration of the second press 1304. Even further, duration of the third press may be less than the duration of the first press 1302 and/or the duration of the second press 1304.

In an embodiment, the detected first press 1302 and/or second press 1304 activate the above mentioned functionalities respectively, when the display 452 is displaying the time menu element 1102. Thus, for example, if the first press 1302 is detected when the display 452 is displaying some other menu element, the synchronization may not be necessarily activated.

Figure 14:
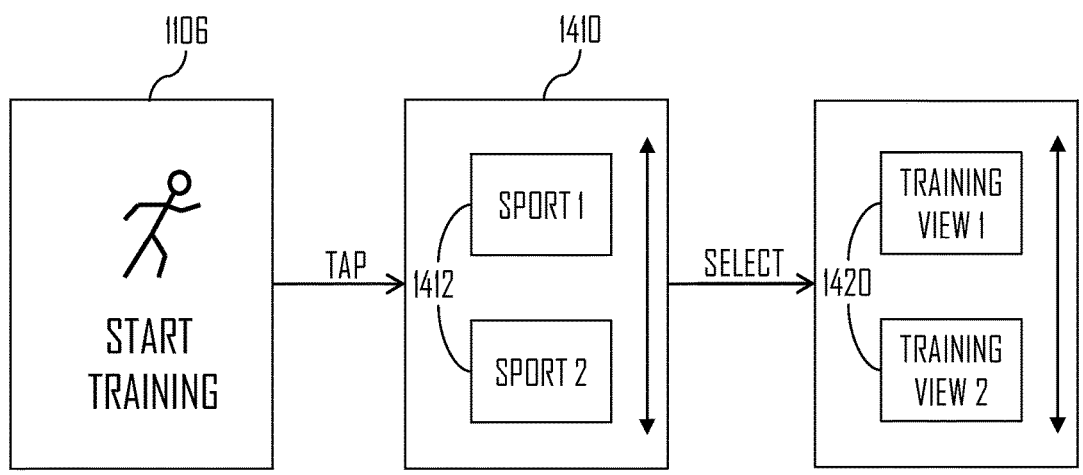
FIG. 14 illustrates an embodiment.

FIG. 14 illustrates an embodiment of the invention. Referring to FIG. 14, the menu element 1106 may be shown. The menu element 1106 may be a training menu element 1106 which may be selected when a physical activity is wanted to be started. When the training menu element 1106 is selected, a physical activity selection menu 1410 may be shown by the display 452. The physical activity selection menu 1410 may comprise one or more physical activities and/or sports 1412 to select from. The one or more physical activities and/or sports 1412 may be scrolled on the display 452, and the wanted physical activity and/or sport 1412 may be selected. The selection may cause the electronics module 250 to start recording of the physical activity performed by the user 100. Thus, for example, sensor(s) related to that physical activity may be activated. In an embodiment, the optical heart rate sensor is activated when the physical activity and/or sport is selected. By pressing the at least one button in the physical activity selection menu 1410 may cause the display 452 to display the previous menu element, e.g. the training menu element 1106. The electronics module 250 may enable the user 100 to select which sensor(s) are turned on when a certain sport and/or physical activity is started. For example, the user 100 may select that optical heart activity sensor and/or GPS sensor are on when a running exercise is started. Thus, the electronics module 250 may turn said sensor(s) on when the running exercise is selected by the user 100, and the recording is started.

In an embodiment, the optical heart activity measurement is deactivated by pressing the display 452 for or over a predetermined time when the electronics module 250 is in the physical activity selection mode 1410. The deactivation may mean that the optical heart activity sensor is deactivated and/or not activated when the recording of the physical activity is started. The predetermined time may be, for example, one second and/or two seconds. In an embodiment, the electronics module prompts whether or not to deactivate the optical heart rate measurement when the display 452 is pressed for or over the predetermined time when the electronics module 250 is in the physical activity selection mode 1410.

In an embodiment, said predetermined time is 2 seconds. The predetermined time may be, for example, 0.5 seconds, 1 second, 3 second and/or 5 seconds, to name a few examples.

The selection of the physical activity and/or sport may cause the display 452 to display one or more training views 1420 related to the selected physical activity and/or sport. The display 452 may display, for example, one training view at a time and/or the user 100 may scroll the display 452 to change the displayed training view. Different physical activity related information may be displayed in each of the one or more training views 1420. For example, one training view may display heart rate and calorie consumption whereas another training view may display speed and/or distance travelled.

If the at least one button is pressed in the one or more training views 1420, the physical activity recording may be paused. A pause view may then be displayed on the display 452, in which the user 100 may be prompted to decide whether to stop or continue the physical activity recording. Pausing may mean, for example, that the sensor(s) are kept on, but no data is recorded when the recording is paused.

In an embodiment, if the electronics module 250 detects that the display 452 is pressed for or over a predetermined time (i.e. 0.5 seconds, 1 second, 2 seconds, or 3 seconds) when the display 452 is displaying the one or more training views 1420, the electronics module 250 activates a heart rate zone lock. When the heart rate zone lock is activated, the electronics module 250 may detect the current heart rate zone (i.e. five heart rate zones) on which the current heart rate of the user 100 is, and give instructions, to the user 100, how to stay on that particular heart rate zone. For example, one heart rate zone may comprise heart rates which are between 100 beats per minute (bpm) and 135 bpm. The instructions may comprise visual, audio and/or haptic indications. For example, one vibration and/or beep may mean that current heart rate is under the heart rate zone lower limit whereas two vibrations and/or beeps may indicate that the current heart rate is over the heart rate zone upper limit.

In an embodiment, the electronics module 250 is configured to cause displaying (i.e. using the display 452) of a plurality of menu elements (i.e. menu elements 1102, 1104, 1106). The electronics module 250 may detect user input and/or user selection, and cause displaying of a view based on the selected menu element. For example, the user 100 may select training menu element 1106, the electronics module 250 may detect the selection, and cause displaying of training view. As described, the selection may be done in different ways, such as swiping or tapping the display 452.

In an embodiment, the electronics module 250 comprises the at least one button. The electronics module 250 may detect that the user 100 presses the at least one button and cause a function to be performed based on duration of the press and/or currently displayed view. For example, when the electronics module 250 is displaying the training view, the at least one button may cause a different function to be performed compared to a situation where the time view is displayed.

In an embodiment, the electronics module 250 is configured to detect duration of a press of the at least one button. Similarly, the electronics module 250 may be configured to detect duration of a press of the display 452. Further, the electronics module 250 may detect which part of the display 452 is pressed. The electronics module 250 may detect that the user 100 presses the display 452 and cause a function to be performed based on duration of the press, currently displayed view, and/or which part of the display 452 is pressed. The function may, for example, be prompting the user 100 whether to stop or continue the current training. The electronics module 250 may further detect user input to the prompting, and cause stopping or continuing the current training based on the user input. For example, if the training is stopped, at least one sensor may be turned off and/or put to sleep mode.

It further needs to be noted that some embodiments described in relation to electronics module 250 may be also carried out by a wrist device that may comprise a wristband and electronics module forming an integral entity. That is, the modularity of the wrist device 102 may not be required, for example, to detect gestures. However, the modularity may be used in some examples. For example, when the user 100 starts to ride a bicycle, he/she may attach the electronics module 250 to the bike instead of his/her wrist. This way, the information on the electronics apparatus may be easier to monitor. The bicycle may comprise a holder for the electronics module 250. In an embodiment, the electronics module 250 is usable with an external display. For example, the bicycle may comprise the external display on which information of the electronics module 250 and/or information viewable on the electronics module 250 may be displayed. The external display may connected wired and/or wirelessly to the electronics module 250.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments, or operations thereof.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the functionalities according to any one of the embodiments or operations thereof may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory and/or transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A wristband comprising:
a first portion;
a second portion; and
a third portion, the third portion being situated between the first and second portions, the first, second and third portions forming one integral entity being elastic, wherein the first and second portions are configured to be mechanically connected to each other in order to enable detachable and adjustable attachment of the wristband to a wrist of a user,
and wherein the third portion comprises a holder configured to enable detachable mounting of an electronics module to the wristband, the electronics module being capable of optical heart activity measurement, the holder being adapted and dimensioned to produce a spring force to the electronics module in order to keep the electronics module in the holder, and to enable the electronics module, when mounted to the wristband, to stiffen a structure of the third portion in order to enable the wristband to firmly attach against the wrist of the user and to enable the optical heart activity measurement with the electronics module,
the holder further comprising a hollow for receiving a multifunction button of the electronics module and a protrusion arranged together with the hollow, the at least one hollow being dimensioned such that inner dimensions of the hollow are substantially the same as outer dimensions of the multifunction button, the protrusion indicating where the multifunction button is located when the electronics module is inserted into the holder, the protrusion and the hollow configured to enable mechanical energy transfer from the protrusion to the multifunction button of the electronics module,
the holder further comprising first and second mounting elements being less elastic compared with the first, second, and third portions, the first and second mounting elements enabling firm attachment of the electronics module to the wristband.

2. The wristband of claim 1, further comprising:
at least one pin situated at the first portion, the at least one pin comprising at least one bulge; and
at least one opening situated at the second portion, wherein the at least one pin is configured to at least partially penetrate the at least one opening, the at least one bulge being adapted and dimensioned such that the at least one bulge detachably locks the at least one pin to the at least one opening.

3. The wristband of claim 2, wherein the at least one bulge comprises a first bulge, the first bulge adapted and dimensioned to detachably lock the at least one pin to the at least one opening of the second portion, wherein the first bulge is situated at one head of the at least one pin, and wherein a base plate is situated in a opposite head of the at least one pin.

4. The wristband of claim 3, wherein the at least one bulge further comprises a second bulge, and the at least one opening of the first portion comprises a second hollow arranged on the opposite side of the first portion compared to the side of a first hollow, the second bulge enabled to penetrate the at least one opening of the first portion, wherein the second hollow is adapted and dimensioned to receive the second bulge, and wherein at least one pin is enabled to be attached to the first portion such that at least a part of the first portion is situated between the base plate and the second bulge.

5. The wristband of claim 2, wherein the second portion comprises a groove situated at an end of the second portion, the groove being adapted and dimensioned to enable the at least one pin to slide through the buckle.

6. The wristband of claim 1, wherein the wristband comprises friction elements causing friction between the first portion and the second portion, when the first and second portions are connected to each other.

7. The wristband of claim 1, wherein the holder is adapted and dimensioned to at least partially surround the electronics module.

8. An electronics module comprising:
an optical heart activity circuitry configured to measure heart activity of a user;
a processing circuitry configured to obtain heart activity measurement data, and to process said data into a heart activity metric characterizing a heart activity of the user; and
a body enclosing at least partly the optical heart activity circuitry and the processing circuitry, the body configured to enable mounting of the electronics module to a holder of a wristband, the body being adapted and dimensioned so that, when mounted to the holder, a measuring head of the optical heart activity circuitry is enabled to be placed against a wrist of the user,
the electronics module further comprising a multifunction button, wherein the multifunction button is configured to be received by a hollow of the holder having a protrusion arranged together with the hollow, the at least one hollow being dimensioned such that inner dimensions of the hollow are substantially the same as outer dimensions of the multifunction button, the protrusion indicating where the multifunction button is located when the electronics module is inserted into the holder, the protrusion and the hollow for enabling mechanical energy transfer from the protrusion to the multifunction button of the electronics module,
wherein the electronics module is configured to firmly attach to the holder using first and second mounting elements of the holder, the first and second mounting elements being less elastic compared with first, second, and third portions of the wristband.

9. The electronics module of claim 8, further comprising:
a communication circuitry configured to enable communication with an external device; and
an antenna structure electrically coupled with the communication circuitry, the antenna structure being situated on at least one edge area of the electronics module.

10. The electronics module of claim 9, wherein the communication circuitry comprises a Bluetooth circuitry, and wherein the antenna structure comprises a Bluetooth antenna.

11. The electronics module of claim 8, further comprising:
an input interface configured to enable wireless charging of the electronics module.

12. The electronics module of claim 8, further comprising:
a user interface configured to enable the user to interact with the electronics module.

13. The electronics module of claim 12, wherein the user interface comprises a touch display.

14. The electronics module of claim 13, wherein the processing circuitry is configured to perform operations comprising:
   determining that the electronics module is not used for a predetermined time; and
   based on the determination, performing at least one of dimming the touch display, turning off the touch display.

15. The electronics module of claim 13, wherein the antenna structure is comprised in at least one edge area of the touch display.

16. The electronics module of claim 13, wherein the touch display is configured to display at least one menu element of a plurality of menu elements, and wherein the displayed at least one menu element is enabled to be changed by scrolling the touch display.

17. The electronics module of claim 16, wherein the plurality of menu elements comprises a time menu element, and wherein the processing circuitry is configured to perform operations comprising:
   detecting that the time menu element is selected by scrolling the touch display; and
   causing the touch display to automatically display time when the time menu element is selected.

18. The electronics module of claim 16, wherein the plurality of menu elements is enabled to be scrolled in an endless loop.

19. The electronics module of claim 8, wherein pressing the multifunction button causes at least one of the following: switching the electronics module on, switching the electronics module off, pairing the electronics module with the external device, changing of a current display element to a previous display element, pausing a physical activity recording, stopping the physical activity recoding.

20. The electronics module of claim 8, wherein the body comprises at least one groove enabling embedding the electronics module into the holder of the wristband.

21. The electronics module of claim 8, wherein the body comprises an alignment element corresponding to an alignment hollow of the holder of the wristband, the alignment element enabling alignment of the electronics module to the holder.

22. The electronics module of claim 8, further comprising:
   a motion circuitry configured to measure motion of the user, wherein the processing circuitry is further configured to obtain the motion measurement data, and to process said data into a motion metric characterizing a motion of the user.

23. The electronics module of claim 8, wherein the processing circuitry is configured to:
   obtain at least one of the heart activity measurement data, the motion measurement data; and
   determine intensity of the physical activity performed by the user based on the obtained data.

24. The electronics module of claim 23, wherein the processing circuitry is further configured to perform operations comprising:
   causing the touch display to display the intensity zone times of the plurality of intensity zones.

25. The electronics module of claim 8, wherein the processing circuitry is configured to perform operations comprising:
   detecting at least one gesture performed by the user; and
   based on the detected at least one gesture, causing a function to be performed on the electronics module.

26. The electronics module of claim 25, wherein the function comprises displaying the heart activity metric on the touch display.

27. The electronics module of claim 25, wherein the function comprises at least one of the functions of the multifunction button.

28. The electronics module of claim 25, wherein the function comprises scrolling the touch display of the electronics module.

29. The electronics module of claim 8, wherein the processing circuitry is configured to perform operations comprising:
   determining that the user is exercising;
   detecting the at least one gesture; and
   causing the touch display to display the heart activity metric.

30. The electronics module of claim 8, further comprising:
   an indication element configured to indicate an event to the user of the electronics module using at least one of a haptic indication, sound indication, visual indication.

31. A wrist device comprising:
   a wristband being substantially elastic and forming one integral entity, the wristband comprising a first, second and third portions, the third portion being situated between the first and second portions, wherein the first and second portions are configured to mechanically connect to each other in order to enable detachable and adjustable attachment of the wrist device to a wrist of a user; and
   an electronics module comprising an optical heart activity sensor configured to measure heart activity of the user and a processing circuitry configured to obtain heart activity measurement data from the optical heart activity sensor, and to process said data into a heart activity metric characterizing a heart activity of the user, the electronics module further comprising a multifunction button,
   wherein the third portion of the wristband comprises a holder configured to enable detachable mounting of the electronics module to the wristband, the holder and the electronics module being adapted and dimensioned so that the holder produces a spring force to the electronics module in order to keep the electronics module in the holder, the electronics module, when mounted to the wristband, stiffening a structure of the third portion in order to enable the wrist device to firmly attach against the wrist of the user and to enable the optical heart activity measurement by the electronics module,
   the holder further comprising a hollow for receiving the multifunction button of the electronics module and a protrusion arranged together with the hollow, the at least one hollow being dimensioned such that inner dimensions of the hollow are substantially the same as outer dimensions of the multifunction button, the protrusion indicating where the multifunction button is located when the electronics module is inserted into the holder, the protrusion and the hollow configured to enable mechanical energy transfer from the protrusion to the multifunction button of the electronics module,
   the holder further comprising first and second mounting elements being less elastic compared with the first, second, and third portions, the first and second mounting elements enabling firm attachment of the electronics module to the wristband.

* * * * *